(12) United States Patent
Zhang

(10) Patent No.: US 8,466,191 B2
(45) Date of Patent: *Jun. 18, 2013

(54) PYRROLINE DERIVATIVES AGAINST CELL RELEASING TUMOR NECROSIS FACTOR, PREPARATION METHODS AND USES THEREOF

(76) Inventor: Hesheng Zhang, Tianjin (CN)

(*) Notice: Subject to any disclaimer, the term of this patent is extended or adjusted under 35 U.S.C. 154(b) by 613 days.

This patent is subject to a terminal disclaimer.

(21) Appl. No.: 12/514,672

(22) PCT Filed: Oct. 16, 2007

(86) PCT No.: PCT/CN2007/002965
§ 371 (c)(1),
(2), (4) Date: Jan. 20, 2010

(87) PCT Pub. No.: WO2008/058448
PCT Pub. Date: May 22, 2008

(65) Prior Publication Data
US 2010/0179189 A1    Jul. 15, 2010

(30) Foreign Application Priority Data
Nov. 15, 2006 (CN) .......................... 2006 1 0129421

(51) Int. Cl.
*A61K 31/407* (2006.01)
*C07D 495/06* (2006.01)

(52) U.S. Cl.
USPC .......................................... 514/421; 548/453

(58) Field of Classification Search
USPC .......................................... 514/421; 548/453
See application file for complete search history.

(56) References Cited

U.S. PATENT DOCUMENTS 5,334,596 A * 8/1994 Hartman et al. .......... 514/301
2006/0199836 A1* 9/2006 Turtle et al. .................... 514/301

FOREIGN PATENT DOCUMENTS

| EP | 467206 | * | 1/1992 |
| WO | WO/99/46267 | * | 9/1999 |
| WO | WO/00/35913 | * | 6/2000 |

OTHER PUBLICATIONS

Nielson et al., Org. Letters, (2004), vol. 6(19). pp. 3381-3384; Pomerantz.*
Pomerantz, Tetrahed. Letters, (2003) vol. 44(8), pp. 1563-1565.*
Pomerantz et al., Synthetic Metals (2003) vol. 135-136, 257-258.*

* cited by examiner

*Primary Examiner* — Taofiq A Solola
(74) *Attorney, Agent, or Firm* — Matthias Scholl P.C.; Matthias Scholl

(57) ABSTRACT

Compounds represented by Formula (I) or Formula (II) against cell releasing TNFα, their pharmaceutically acceptable salts or hydrates and preparation methods and uses thereof, in which A and B represent $CH_2$, CO, SO, or $SO_2$; D represents S, NH, or $NC_{1-6}$ alkyl; $R^1$ represents H, or one or two same or different radical(s) selected from the group consisting of F, Cl, Br, $C_{1-4}$ alkyl, OH, $OC_{1-4}$ alkyl, $NO_2$, NHC(O)$C_{1-4}$ alkyl, $NH_2$, NH($C_{1-4}$ alkyl), or N($C_{1-4}$ alkyl)$_2$.

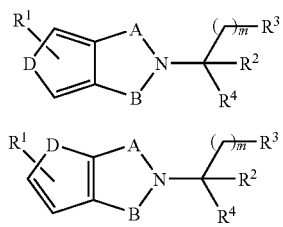

20 Claims, No Drawings

PYRROLINE DERIVATIVES AGAINST CELL RELEASING TUMOR NECROSIS FACTOR, PREPARATION METHODS AND USES THEREOF

FIELD OF THE INVENTION

The invention relates to pyrroline-dione derivatives which inhibit the release of tumor necrosis factor (TNF) in cells, a method of their preparation, and a method of using the same as pharmaceutical agents.

BACKGROUND OF THE INVENTION

Tumor necrosis factor-alpha (TNFα) is a cytokine, mainly produced by mononuclear macrophages. It causes inflammation, fever, cardiovascular dysfunction, hemorrhage, blood coagulation and a series of acute reactions similar to acute infection and shock when administered to humans and animals. Moreover, excessive or uncontrolled levels of TNFα in animals or humans often indicates one of the following diseases:
1) Endotoxaemia and/or toxic shock syndrome (Tracey et al., Nature 330, 662-4 1987; Hinshaw et al., Circ Shock 30, 279-92 (1990));
2) Cachexia (Dezube et al., Laucet, 335(8690), 662 (1990)); or
3) Adult Respiratory Distress Syndrome (ARDS) (Millar et al., Laucet 2(8665), 712-714 (1989)).

TNFα also plays an important role in bone resorption diseases including arthritis (Betolinni et al., Nature 319, 516-8 (1986)). Furthermore, experiments in vitro and vivo have shown TNFα may stimulate bone resorption by stimulating the formation and activation of osteoclasts and resist the formation of bone tissue.

At present, the disease most commonly linked to TNFα released by tumor and host tissue is hypercalcemia, which is closely related to malignant tumors (Calci. Tissue Int. (US) 46(Suppl.), S3-10 (1990)). It has also been observed that immune response is closely related to an increased serum concentration of TNFα in patient after bone marrow transplantation (Holler et al., Blood, 75(4), 1011-1016 (1990)).

Fatal hyperacute neurogenic syndrome brainstem-type malaria, the most dangerous type of malaria, is also linked to high blood levels of TNFα. When this kind of malaria occurs, the levels of TNFα in serum are directly related to the disease, which often occurs during an acute attack of malaria in patients (Grau et al., N. Engl. J. Med. 320(24), 1586-91 (1989)).

TNFα also plays an important role in chronic pneumonia. The storage of silicon-containing particles can cause silicosis. Silicosis is a type of progressive respiratory failure, resulting from fibrosis of pulmonary tissues. In an animal pathological model, a TNFα antibody can fully block the progress of lung fibrosis in mice caused by silica dust (Pignet et al., Nature, 344:245-7 (1990)). It was also discovered that TNFα levels are abnormally high in serum of animals with pulmonary fibrosis caused by silica dust or asbestos dust in animal experiments (Bissonnette et al., Inflammation 13(3), 329-339 (1989)). Pathological research reveals that TNFα levels in pulmonary tissues of patients with pulmonary sarcoidosis is much higher than that of healthy people (Baughman et al., J. Lab. Clin. Med. 115(1), 36-42 (1990)). This suggests that TNFα inhibitor may have a great significance in the treatment of chronic pulmonary diseases and lung injury.

One reason for inflammation occurring in the patient with reperfusion injury may be abnormal levels of TNFα, and TNFα is regarded as the chief cause inducing tissue injury caused by ischemia (Uadder et al., PNAS 87, 2643-6 (1990)).

Besides, it has been shown that TNFα may start retroviral replication comprising that of HIV-1 (Duh et al., Proc. Nat. Acad. Sci., 86, 5974-8 (1989)). T-cells need to be activated before HIV invades them. Once the activated T-cells are infected by virus (HIV), those T-cells must remain in an activated state so that the HIV virus genes are able to express and/or replicate successfully. Cytokines, especially TNFα, play an important role in the process of HIV protein expression or viral replication regulated by T-cells. Therefore, inhibition of TNFα production can in turn inhibit HIV replication in T-cells (Poll et al., Proc. Nat. Acad. Sci., 87, 782-5 (1990); Monto et al., Blood 79,2670 (1990); Poll et al., AIDS Res. Human Retrovirus, 191-197 (1992)).

cAMP can regulate many functions of cells, such as inflammation response, comprising asthma, and inflammation (Lome and Cheng, Drugs of the future, 17(9), 799-807, 1992). When inflammation occurs, increased cAMP concentration in white cells inhibits activation of white cells, and then releases inflammation regulatory factors including TNFα so as to exacerbate inflammation in patients. Consequently, the inhibition of TNFα release can alleviate inflammation diseases including asthma.

Yu Yanyan et al, have found that TNFα plays an important role in the process of liver necrosis in patients with viral hepatitis. (Yu Yanyan etc., Chinese Journal of Internal Medicine 1996, 35:28-31). This indicates that TNFα inhibitors may play a great role in treatment of chronic hepatic disease and liver injury.

Li Yingxu et al have found that levels of synthesis and secretion of tumor necrosis factors in monocytes in the peripheral blood of patients with chronic hepatic disease increase, which induces secretion of other cytokines (for example, IL-1β, IL-6 and IL-8). All these cytokines including tumor necrosis factors are all together involved in the injury process of hepatocytes (Journal of Qiqihar Medical Colleg, 22(10):1119-1120, 2001). Their study results coincide with the conclusions of Yoshioka, et al. (Hepatology, 1989, 10:769-777) and Wang Xin, et al. (Chinese Journal of Infectious Diseases, 1997, 15(2):85-88). It has also been found that thalidomide, an inhibitor of TNFα, is able to inhibit TNFα secretion of monocytes in the peripheral blood of hepatitic patients, which lays a foundation for the application of TNFα inhibitors for treatment of hepatitis, cirrhosis, and liver cancer.

By promoting biosynthesis and release of inflammatory cytokines (Abboud H. E. Kidney Int. 1993, 43: 252-267), increasing expression of cellular adhesion molecules (Egido J. et al, Kidney Int. 1993, 43(suppl 39): 59-64), and stimulating biosynthesis and release of prostaglandin G2 (PGG2) and platelet-activating factor (PAF) (Cammusi G. et al, Kidney Int., 43(suppl 39): 32-36), TNFα may induce a series of inflammatory responses, including aggregation and adhesion of inflammatory cells, increase dilation and permeability of blood capillaries, induce fever, increase the amount of neutrophilic granulocytes in blood circulation, and change hemodynamics. All of this may lead to injury of renal cells. Many studies have suggested that oTNFα plays an important role in breakout and deterioration of nephritis.

TNFα is involved in the regulation of immune functions by means of activation of macrophages, immunological stimulation of proliferation of T-lymphocytes, regulating the differentiation of B lymphocytes and enhancing the cytotoxicity of natural killer cells (NK). Therefore, decreasing TNFα levels and/or increasing cAMP levels constitutes an effective way for treatment of many inflammatory, infectious, immune or malignant tumor diseases, including but not limited to septic shock, endotoxic shock, hemodynamic shock, septic syndrome, post ischemic reperfusion injury, malaria, mycobacterial infection, meningitis, psoriasis, congestive heart failure, fibrotic disease, cachexia, transplant immune rejection, cancer, autoimmune disease, opportunistic infection in AIDS, rheumatoid arthritis (RA), hepatitis, nephritis, rheumatoid spondylitis, and so on.

In recent years, TNFα antibodies have made breakthrough progress in the clinical treatment of arthritis, and become an indispensable main drug in the treatment of arthritis. However, antibody drugs have disadvantages such as high price, difficult production, and immunotoxicity. Accordingly, research and development on small molecule TNFα inhibitors with low toxicity and high efficiency is of great social benefit and has high economic value.

BRIEF SUMMARY OF THE INVENTION

In view of the above-described problems, it is one objective of the invention to provide a compound or pharmaceutically acceptable salt or hydrate thereof which inhibits the release of TNFα in cells.

It is another objective of the invention to provide a pharmaceutical preparation comprising a compound or pharmaceutically acceptable salt or hydrate thereof which inhibits the release of TNFα in cells.

It is still another objective of the invention to provide a method of preparing a compound which inhibits the release of TNFα in cells.

To achieve the above objectives, in accordance with one embodiment of the invention, provided is a compound of Formula (I) or Formula (II),

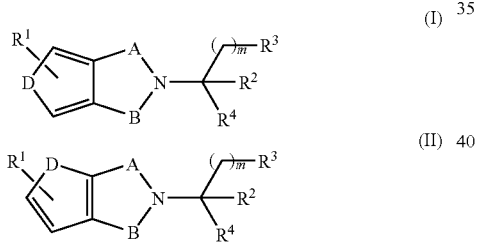

wherein

A and B independently represent $CH_2$, CO, SO, or $SO_2$;

D represents S, NH, or $NC_{1-6}$ alkyl;

$R^1$ represents H, or one or two same or different occurrences of F, Cl, Br, $C_{1-4}$alkyl, OH, $OC_{1-4}$alkyl, $NO_2$, NHC(O)$C_{1-4}$alkyl, $NH_2$, $NH(C_{1-4}$alkyl), or $N(C_{1-4}$alkyl)$_2$;

$R^2$ at each occurrence represents F, $CF_3$, H, or $C_{1-4}$alkyl;

$R^3$ at each occurrence represents F, Cl, H, $C_{1-4}$alkyl, OH, $CH(OH)C_{1-4}$alkyl, $OC_{1-4}$alkyl, $NHC(O)C_{1-4}$alkyl, $NH_2$, $NH(C_{1-4}$alkyl), $N(C_{1-4}$alkyl)$_2$, $C(O)OC_{1-4}$alkyl, $C(O)NH_2$, $C(O)NH(C_{1-4}$alkyl), $C(O)N(C_{1-4}$alkyl)$_2$, C(O)NHOH, $C(O)NH(OC_{1-4}$alkyl), $C(O)C_{1-4}$alkyl, $S(O)C_{1-4}$alkyl, $SO_2C_{1-4}$alkyl, $SO_2NHC_{1-4}$alkyl, $NHSO_2C_{1-4}$alkyl, $O_2CC_{1-4}$alkyl, $NHC(O)C_{1-4}$alkyl, CN, CH=NOH, CH=N($OC_{1-4}$alkyl), $C(C_{1-4}$alkyl)=NOH, $C(C_{1-4}$alkyl)=N($OC_{1-4}$alkyl), CH=NCN, CH=NC(O)$C_{1-4}$alkyl, CH=C(CN)$_2$, CH=CHNO$_2$, C(=NH)NH($C_{1-4}$alkyl), $C(C_{1-4}$alkyl)=NCN, $C(C_{1-4}$alkyl)=NC(O)$C_{1-4}$alkyl, $C(C_{1-4}$alkyl)=C(CN)$_2$, or $C(C_{1-4}$alkyl)=CHNO$_2$;

$R^4$ represents H, $C_{1-8}$alkyl, or $(CH_2)_nAr$—$R^5$, and Ar represents a 4- to 8-membered hydrocarbon ring or aromatic ring containing from 0 to 4 heteroatoms;

$R^5$ represents H, or 1 to 4 same or different occurrences of F, $CF_3$, CN, Cl, $C_{1-4}$alkyl, OH, $OC_{1-4}$alkyl, NHC(O)$C_{1-4}$alkyl, $NH_2$, $NH(C_{1-4}$alkyl), $N(C_{1-4}$alkyl)$_2$, $C(O)OC_{1-4}$alkyl, $OOCC_{1-4}$alkyl, $C(O)NH_2$, $C(O)NH(C_{1-4}$alkyl), $C(O)N(C_{1-4}$alkyl)$_2$, $C(O)C_{1-4}$alkyl, $S(O)C_{1-4}$alkyl, $SO_2C_{1-4}$alkyl, $O_2CC_{1-4}$alkyl, E, or W—$(CH_2)_lE$;

E represents a 4- to 8-membered hydrocarbon ring or aromatic ring containing from 0 to 4 heteroatoms;

W represents O, S, NH, or $CH_2$;

l represents 0, 1, 2, 3 or 4;

m represents 0, 1, 2, 3, 4, 5 or 6; and n represents 0, 1, 2, 3 or 4.

An aromatic ring represented by Ar or E is selected from the group consisting of phenyl, naphthalyl, pyridyl, pyrimidinyl, thiophene, furyl, indolyl, isoindolyl, benzothiophenyl, benzofuryl, or a compound of Formula (III), Formula (IV), or Formula (V), wherein X represents O or S.

A hydrocarbon ring represented by Ar or E is a cyclopentantyl, cyclohexyl, or a heterocyclyl of Formula (VI), wherein G represents O, S, or $NR^6$; Y represents 1,2-ethylidene, 1,3-propylidene, 1,4-butylene, 1,5-pentylene, 1,6-hexylidene, $CH_2OCH_2$, $CH_2SCH_2$, or $CH_2NR^7CH_2$, and $R^6$ and $R^7$ independently represent H or $C_{1-4}$alkyl.

In certain embodiments of the invention, $C_{1-4}$alkyl is a straight-chain or a branched-chain alkyl, and is optionally substituted with F, CN, OH, COOH, $C(O)NH_2$, $NHC(O)R^8$, $NR^8R^9$, $NHC(O)NH_2$, $NHC(NH)NH_2$, $OR^8$, or $SR^9$, wherein $R^8$ and $R^9$ independently represent H or $C_{1-4}$alkyl.

In certain embodiments of the invention, $C_{1-4}$alkyl, $C_{1-6}$alkyl, and $C_{1-8}$alkyl are straight chain alkyl or branched chain alkyl, and may be substituted with F, CN, OH, COOH, $C(O)NH_2$, $NHC(O)R^8$, $NR^8R^9$, $NHC(O)NH_2$, $NHC(NH)NH_2$, $OR^8$, or $SR^9$, wherein $R^8$ and $R^9$ independently represent H or $C_{1-4}$alkyl.

In one embodiment of the invention, provided are methods of inhibiting the release of TNFα in peripheral blood mononuclear cells (PBMCs) stimulated by lipopolysaccharide (LPS) by a compound represented by Formula (I) or Formula (II). Experimental results are listed in Table 1. The results show the activity of most compounds of the invention is higher than that of thalidomide, a widely-used clinical pharmaceutical composition.

In certain embodiments of the invention, the compounds of Formula (I) or Formula (II) suitable for being used in pharmaceutical composition are the compounds wherein m represents an integer from 1 to 4, and particularly 1, 2 and 3.

In certain embodiments of the invention, the compound of Formula (I) or Formula (II) suitable for being used in a pharmaceutical composition are the compounds wherein 1, and n separately represent an integer from 0 to 3, particularly 0, 1 and 2.

In certain embodiments of the invention, the compound of Formula (I) or Formula (II) suitable for being used in a pharmaceutical composition are the compounds wherein $R^1$ represents H, or one or two same or different occurrences of F, Cl, Br, $CH_3$, $CH_2CH_3$, OH, $OCH_3$, $OCH_2CH_3$, $NH_2$, $NHCH_3$, $NHCH_2CH_3$, or $N(CH_3)_2$, and particularly H, F, or $NH_2$.

In certain embodiments of the invention, the compounds of Formula (I) or (II) suitable for being used in a pharmaceutical composition are the compounds wherein $R^2$ represents H, F or $CH_3$.

In certain embodiments of the invention, the compound of Formula (I) or (II) suitable for being used in a pharmaceutical composition are the compounds wherein $R^3$ represents OH, $CH(OH)CH_3$, $CH(OH)CH_2CH_3$, $OCH_3$, $OCH_2CH_3$, $OCH(CH_3)_2$, $OCH_2CH_2CH_3$, $C(O)CH_3$, $C(O)CH_2CH_3$, $C(O)CH_2CH_2CH_3$, $C(O)CH(CH_3)_2$, $COOCH_3$, $COOCH_2CH_3$, $COOCH_2CH_2CH_3$, $COOCH(CH_3)_2$, $S(O)CH_3$, $S(O)CH_2CH_3$, $SO_2CH_3$, $SO_2CH_2CH_3$, $C(O)NH_2$, $C(O)NHCH_3$, $C(O)NHCH_2CH_3$, $C(O)NHCH_2CH_2CH_3$, $C(O)N(CH_3)_2$, $C(O)NHOH$, $C(O)NH(OMe)$, $C(O)NH(OEt)$, $CN$, $CH=NOH$, $CH=NOMe$, $CH=NOEt$, $CH=NCN$, $CH=NC(O)Me$, $CH=NC(O)Et$, $C(Me)=NOH$, $C(Me)=NOMe$, $C(Me)=NOEt$, $C(Me)=NCN$, $C(Me)=NC(O)Me$, $C(Me)=NC(O)Et$, $CH=C(CN)_2$, $CH=CHNO_2$, $C(Me)=C(CN)_2$, $C(Et)=CHNO_2$, $C(Et)=NOH$, $C(Et)=NOMe$, $C(Et)=NOEt$, $C(Et)=NCN$, or $C(Et)=NC(O)Me$.

In certain embodiments of the invention, the compounds of Formula (I) or (II) suitable for being used in a pharmaceutical composition are the compounds wherein Ar and E independently represent phenyl, naphthalyl, pyridyl, pyrimidinyl, thiophenyl, furyl, indolyl, isoindolyl, benzothiophenyl, or benzofuryl.

In certain embodiments of the invention, the compound of Formula (I) or Formula (II) suitable for being used in a pharmaceutical composition are the compounds wherein $R^5$ represents H, or from 1 to 4 same or different occurrences of F, Cl, methyl, ethyl, trifluoromethyl, OH, $CH_3COO$, $OOCCH_2CH_3$, $OOCCH_2CH_2CH_3$, $OCH_3$, ethoxy, isopropoxy, propoxy, butoxy, cyclopentyloxy, benzoyloxy, phenoxy, pyridyl-methoxy, phenoxyethyl, substituted benzoyloxy, substituted pyridyl-methoxy, substituted phenoxy, substituted phenoxyethyl, NHC(O)Me, NHC(O)Et, $NH_2$, methylamino, ethylamino, dimethylamino, CN, $COOCH_3$, $COOCH_2CH_3$, $COOCH_2CH_2CH_3$, $COOCH(CH_3)_2$, $C(O)NH_2$, $C(O)NHCH_3$, $C(O)NHCH_2CH_3$, $C(O)NHCH_2CH_2CH_3$, or $C(O)N(CH_3)_2$.

When the compound of Formula (I) or (II) is an R/S isomer, it can be an R isomer, or an S isomer, or a mixture of an R isomer and an S isomer.

When the compound of Formula (I) or (II) is defined is an E/Z isomer, it can be an E isomer, or a Z isomer, or a mixture of an E isomer and a Z isomer.

In certain embodiments of the invention, the compound of Formula (I) or Formula (II) suitable for being used as medical active ingredient may be a prodrug or a metabolite of the compound.

The compound of Formula (I) or Formula (II) of the invention suitable for being used as medical active ingredients may be prepared in the form of a free base or an inorganic acid salt, including hydrochloride, sulfate, nitrate, phosphate, or in form of organic salts, comprising sulfonate, acetate, formate, fumarate, maleate, citrate, tartrate, malate, benzoate, ascorbate, gluconate, lactate, succinate, or trifluoroacetate.

In another embodiment of the invention, provided is a method of preparing a compound of Formula (I) or Formula (II),

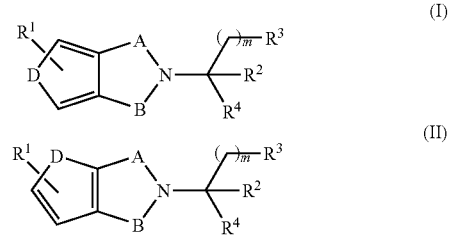

wherein

A and B independently represents $CH_2$, CO, SO, or $SO_2$;

D represents S, NH, or $NC_{1-6}$ alkyl;

$R^1$ represents H, or from 1 to 2 same or different occurrences of F, Cl, Br, $C_{1-4}$alkyl, OH, $OC_{1-4}$alkyl, $NO_2$, NHC(O)$C_{1-4}$alkyl, $NH_2$, $NH(C_{1-4}$alkyl), or $N(C_{1-4}$alkyl)$_2$;

$R^2$ at each occurrence represents F, $CF_3$, H, or $C_{1-4}$alkyl;

$R^3$ at each occurrence represents F, Cl, H, $C_{1-4}$alkyl, OH, $CH(OH)C_{1-4}$alkyl, $OC_{1-4}$alkyl, NHC(O)$C_{1-4}$alkyl, $NH_2$, $NH(C_{1-4}$alkyl), $N(C_{1-4}$alkyl)$_2$, C(O)O$C_{1-4}$alkyl, $C(O)NH_2$, $C(O)NH(C_{1-4}$alkyl), $C(O)N(C_{1-4}$alkyl)$_2$, C(O)NHOH, $C(O)NH(OC_{1-4}$alkyl), $C(O)C_{1-4}$alkyl, $S(O)C_{1-4}$alkyl, $SO_2C_{1-4}$alkyl, $SO_2NHC_{1-4}$alkyl, $NHSO_2C_{1-4}$alkyl, $O_2CC_{1-4}$alkyl, NHC(O)$C_{1-4}$alkyl, CN, CH=NOH, CH=N(OC$_{1-4}$alkyl), C(C$_{1-4}$alkyl)=NOH, C(C$_{1-4}$alkyl)=N(OC$_{1-4}$alkyl), CH=NCN, CH=NC(O)$C_{1-4}$alkyl, CH=C(CN)$_2$, CH=CHNO$_2$, C(=NH)NH(C$_{1-4}$alkyl), C(C$_{1-4}$alkyl)=NCN, C(C$_{1-4}$alkyl)=NC(O)$C_{1-4}$alkyl, C(C$_{1-4}$alkyl)=C(CN)$_2$, or C(C$_{1-4}$alkyl)=CHNO$_2$;

$R^4$ represents H, $C_{1-8}$alkyl, or $(CH_2)_n$Ar—$R^5$, and Ar represents a 4 to 8-membered hydrocarbon ring or an aromatic ring containing from 0 to 4 heteroatoms;

$R^5$ represents H, or 1-4 same or different occurrences of F, Cl, $CF_3$, CN, $C_{1-4}$alkyl, OH, $OC_{1-4}$alkyl, NHC(O)$C_{1-4}$alkyl, $NH_2$, $NH(C_{1-4}$alkyl), $N(C_{1-4}$alkyl)$_2$, C(O)O$C_{1-4}$alkyl, $OOCC_{1-4}$alkyl, $C(O)NH_2$, $C(O)NH(C_{1-4}$alkyl), $C(O)N(C_{1-4}$alkyl)$_2$, $C(O)C_{1-4}$alkyl, $S(O)C_{1-4}$alkyl, $SO_2C_{1-4}$alkyl, $O_2CC_{1-4}$alkyl, E, or W—$(CH_2)_l$E;

E represents a 4 to 8-membered hydrocarbon ring or aromatic ring containing 0 to 4 heteroatoms;

W represents O, S, NH, or $CH_2$;

l represents 0, 1, 2, 3 or 4;

m represents 0, 1, 2, 3, 4, 5, or 6; and n represents 0, 1, 2, 3, or 4;

the method comprising the steps of:

(1) contacting a compound of Formula (VII) or Formula (VIII) with a compound of Formula (IX) to obtain a compound of Formula (X) or Formula (XI),

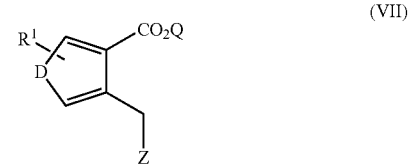

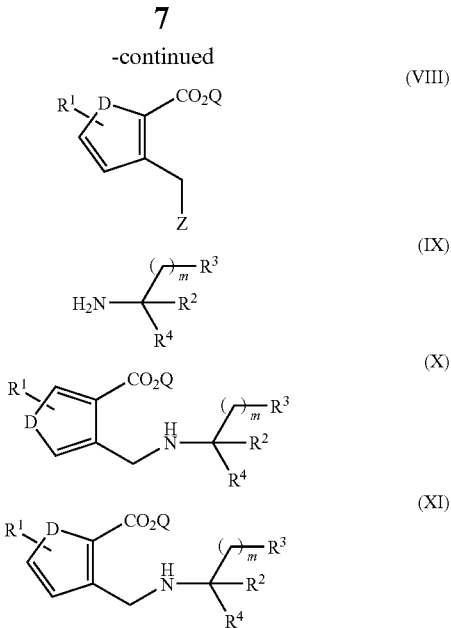

wherein the definitions of D, $R^1$, $R^2$, $R^3$, $R^4$ and m are the same as that for Formula (I) or Formula (II); Z represents Cl, Br, I, Ms or Ts; and Q represents methyl or tert-butyl.

In a class of this embodiment, the molar ratio of the compound of Formula (VII) or Formula (VIII) to the compound of Formula (IX) is between 3:1 and 1:3.

The reaction is facilitated by an inorganic base including but not limited to NaH, KH, $CaH_2$, $K_2CO_3$, $Na_2CO_3$, $KHCO_3$, $NaHCO_3$, $Li_2CO_3$, $Cs_2CO_3$, LiOH, KOH, NaOH, $Ca(OH)_2$, $K_3PO_4$, $K_2HPO_4$, or by an organic base. The proportion of the base to the compound of Formula (VII) or Formula (VIII) is between 50% and 300% by mole.

The reaction is conducted in an organic solvent, such as dichloromethane, chloroform, acetone, butanone, dimethylformamide, dimethylsulfoxide, ethylene glycol dimethyl ether, tetrahydrofurane, pyridine, or acetonitrile, and may be conducted under multi-phase conditions, especially in the presence of a phase-transfer catalyst.

(2) hydrolyzing the compound of Formula (X) or Formula (XI) to obtain a corresponding acid of Formula (XII) or Formula (XIII),

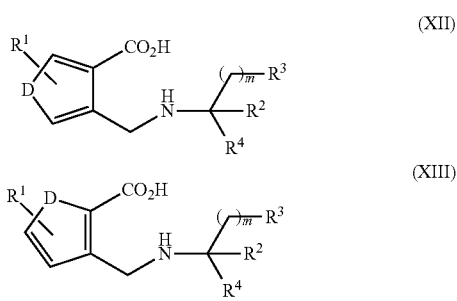

(3) dehydrating and cyclizing the compound of Formula (XII) or Formula (XIII) to obtain the compound of Formula (I) or Formula (II).

The reactions are conducted in an organic solvent, such as dichloromethane, chloroform, acetone, butanone, dimethylformamide, dimethylsulfoxide, ethylene glycol dimethyl ether, tetrahydrofurane, pyridine, or acetonitrile. A condensing agent such as thionyl chloride, DCC, CDI, EDCI may be added, and pyridine derivatives such as DMAP, or 4-(1-pyrroline) pyridine may be added as a catalyst.

In another embodiment provided is another method of preparing a compound of Formula (I) or Formula (II) comprising contacting a compound of Formula (XIV) or Formula (XV) with a compound of Formula (IX) to obtain an intermediate compound, and then dehydrating and cyclizing the intermediate compound to give a compound of Formula (I) or Formula (II), wherein the definitions of D and $R^1$ are the same as that for Formula (I) or Formula (II).

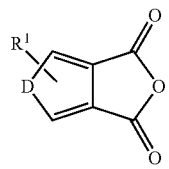

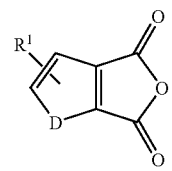

The molar ratio of the compound of Formula (XIV) or Formula (XV) to the compound of Formula (IX) may be between 3:1 and 1:3. The reaction is facilitated by a base including but not limited to NaH, KH, $CaH_2$, $K_2CO_3$, $Na_2CO_3$, $KHCO_3$, $NaHCO_3$, $Li_2CO_3$, $Cs_2CO_3$, LiOH, KOH, NaOH, $Ca(OH)_2$, $K_3PO_4$, $K_2HPO_4$, trimethylamine, triethylamine, diethyl isopropylamine, 4-methylmorpholine, 1-methyl cyclohexylamine, 1-methylpyrroline, or pyridine. The proportion of the base to the compound of Formula (XIV) or Formula (XV) is between 50% and 300% by mole.

The reactions are conducted in an organic solvent, such as dichloromethane, chloroform, acetone, butanone, dimethylformamide, dimethylsulfoxide, ethylene glycol dimethyl ether, tetrahydrofurane, pyridine, or acetonitrile, and may be conducted under multi-phase conditions, especially in the presence of a phase-transfer catalyst.

The dehydration and cyclization reactions of the intermediate compound are conducted in an organic solvent, such as dichloromethane, chloroform, acetone, butanone, dimethylformamide, dimethylsulfoxide, ethylene glycol dimethyl ether, tetrahydrofurane, pyridine or acetonitrile. A condensing agent such as thionyl chloride, DCC, CDI, EDCI may be added, and pyridine derivatives such as DMAP, 4-(1-pyrroline) pyridine may be added as a catalyst.

In another embodiment of the invention, provided is a use of a compound of Formula (I) or Formula (II) for the preparation of a medicine,

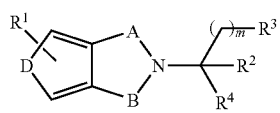

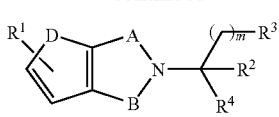
(II)

wherein

A and B independently represent $CH_2$, CO, SO, or $SO_2$;

D represents S, NH, or $NC_{1-6}$ alkyl;

$R^1$ represents H, or one or two same or different occurrences of F, Cl, Br, $C_{1-4}$alkyl, OH, $OC_{1-4}$alkyl, $NO_2$, $NHC(O)C_{1-4}$alkyl, $NH_2$, $NH(C_{1-4}$alkyl$)$, or $N(C_{1-4}$alkyl$)_2$;

$R^2$ at each occurrence represents F, $CF_3$, H, or $C_{1-4}$alkyl;

$R^3$ at each occurrence represents F, Cl, H, $C_{1-4}$alkyl, OH, $CH(OH)C_{1-4}$alkyl, $OC_{1-4}$alkyl, $NHC(O)C_{1-4}$alkyl, $NH_2$, $NH(C_{1-4}$alkyl$)$, $N(C_{1-4}$alkyl$)_2$, $C(O)OC_{1-4}$alkyl, $C(O)NH_2$, $C(O)NH(C_{1-4}$alkyl$)$, $C(O)N(C_{1-4}$alkyl$)_2$, $C(O)NHOH$, $C(O)NH(OC_{1-4}$alkyl$)$, $C(O)C_{1-4}$alkyl, $S(O)C_{1-4}$alkyl, $SO_2C_{1-4}$alkyl, $SO_2NHC_{1-4}$alkyl, $NHSO_2C_{1-4}$alkyl, $O_2CC_{1-4}$alkyl, $NHC(O)C_{1-4}$alkyl, CN, CH=NOH, CH=N($OC_{1-4}$alkyl), $C(C_{1-4}$alkyl$)$=NOH, $C(C_{1-4}$alkyl$)$=N($OC_{1-4}$alkyl), CH=NCN, CH=NC(O)$C_{1-4}$alkyl, CH=C(CN)$_2$, CH=CHNO$_2$, C(=NH)NH($C_{1-4}$alkyl), $C(C_{1-4}$alkyl$)$=NCN, $C(C_{1-4}$alkyl$)$=NC(O)$C_{1-4}$alkyl, $C(C_{1-4}$alkyl$)$=C(CN)$_2$, or $C(C_{1-4}$alkyl$)$=CHNO$_2$;

$R^4$ represents H, $C_{1-8}$alkyl, or $(CH_2)_n$Ar—$R^5$, and Ar represents a 4 to 8-membered hydrocarbon ring or an aromatic ring containing from 0 to 4 heteroatoms;

$R^5$ represents H, or from 1 to 4 same or different occurrences of F, $CF_3$, CN, Cl, $C_{1-4}$alkyl, OH, $OC_{1-4}$alkyl, $NHC(O)C_{1-4}$alkyl, $NH_2$, $NH(C_{1-4}$alkyl$)$, $N(C_{1-4}$alkyl$)_2$, $C(O)OC_{1-4}$alkyl, $OOCC_{1-4}$alkyl, $C(O)NH_2$, $C(O)NH(C_{1-4}$alkyl$)$, $C(O)N(C_{1-4}$alkyl$)_2$, $C(O)C_{1-4}$alkyl, $S(O)C_{1-4}$alkyl, $SO_2C_{1-4}$alkyl, $O_2CC_{1-4}$alkyl, E, or W—$(CH_2)_l$E;

E represents a 4- to 8-membered hydrocarbon ring or an aromatic ring containing from 0 to 4 heteroatoms;

W represents O, S, NH, or $CH_2$;

l represents 0, 1, 2, 3, or 4;

m represents 0, 1, 2, 3, 4, 5, or 6; and n represents 0, 1, 2, 3, or 4.

The diseases or physiological disorders which can be effectively alleviated or treated by decreasing TNFα concentration in patients after administering the pharmaceutical composition comprising the compound of Formula (I) or (II) include but are not limited to inflammatory diseases, infectious diseases, autoimmune diseases or malignant tumors. Specifically, the disease includes but is not limited to septic shock, endotoxic shock, hemodynamic shock, septic syndrome, post ischemic reperfusion injury, malaria, mycobacterial infection, meningitis, psoriasis, congestive heart failure, fibrotic disease, cachexia, transplant immune rejection, cancer, autoimmune disease, opportunistic infection in AIDS, erythema nodosum leprosy, lupus erythematosus, refractory lupus erythematosus, Behcet syndrome, regional ileitis, myelodysplastic syndrome, rheumatoid arthritis (RA), hepatitis, nephritis, rheumatoid spondylitis, multiple myeloma, thyroid tumor, kidney cancer, prostate cancer, lymphoma, leukemia, liver cancer, brain glioma, colorectal cancer, lung cancer, stomach cancer, breast cancer, melanoma, cervical cancer, pancreatic cancer, esophageal cancer, oral cancer, throat cancer, and rhinocarcinoma.

In another aspect, the invention provides a pharmaceutical composition comprising a compound of Formula (I) or Formula (II),

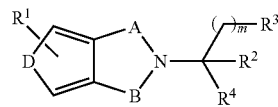
(I)

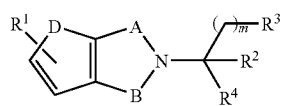
(II)

wherein

A and B independently represents $CH_2$, CO, SO, or $SO_2$;

D represents S, NH, or $NC_{1-6}$ alkyl;

$R^1$ represents H, or one or two same or different occurrences of F, Cl, Br, $C_{1-4}$alkyl, OH, $OC_{1-4}$alkyl, $NO_2$, $NHC(O)C_{1-4}$alkyl, $NH_2$, $NH(C_{1-4}$alkyl$)$, or $N(C_{1-4}$alkyl$)_2$;

$R^2$ at each occurrence represents F, $CF_3$, H, or $C_{1-4}$alkyl;

$R^3$ at each occurrence represents F, Cl, H, $C_{1-4}$alkyl, OH, $CH(OH)C_{1-4}$alkyl, $OC_{1-4}$alkyl, $NHC(O)C_{1-4}$alkyl, $NH_2$, $NH(C_{1-4}$alkyl$)$, $N(C_{1-4}$alkyl$)_2$, $C(O)OC_{1-4}$alkyl, $C(O)NH_2$, $C(O)NH(C_{1-4}$alkyl$)$, $C(O)N(C_{1-4}$alkyl$)_2$, $C(O)NHOH$, $C(O)NH(OC_{1-4}$alkyl$)$, $C(O)C_{1-4}$alkyl, $S(O)C_{1-4}$alkyl, $SO_2C_{1-4}$alkyl, $SO_2NHC_{1-4}$alkyl, $NHSO_2C_{1-4}$alkyl, $O_2CC_{1-4}$alkyl, $NHC(O)C_{1-4}$alkyl, CN, CH=NOH, CH=N($OC_{1-4}$alkyl), $C(C_{1-4}$alkyl$)$=NOH, $C(C_{1-4}$alkyl$)$=N($OC_{1-4}$alkyl), CH=NCN, CH=NC(O)$C_{1-4}$alkyl, CH=C(CN)$_2$, CH=CHNO$_2$, C(=NH)NH($C_{1-4}$alkyl), $C(C_{1-4}$alkyl$)$=NCN, $C(C_{1-4}$alkyl$)$=NC(O)$C_{1-4}$alkyl, $C(C_{1-4}$alkyl$)$=C(CN)$_2$, or $C(C_{1-4}$alkyl$)$=CHNO$_2$;

$R^4$ represents H, $C_{1-8}$alkyl, or $(CH_2)_n$Ar—$R^5$, and Ar represents a 4- to 8-membered hydrocarbon ring or an aromatic ring containing from 0 to 4 heteroatoms;

$R^5$ represents H, or from 1 to 4 same or different occurrences of F, $CF_3$, CN, Cl, $C_{1-4}$alkyl, OH, $OC_{1-4}$alkyl, $NHC(O)C_{1-4}$alkyl, $NH_2$, $NH(C_{1-4}$alkyl$)$, $N(C_{1-4}$alkyl$)_2$, $C(O)OC_{1-4}$alkyl, $OOCC_{1-4}$alkyl, $C(O)NH_2$, $C(O)NH(C_{1-4}$alkyl$)$, $C(O)N(C_{1-4}$alkyl$)_2$, $C(O)C_{1-4}$alkyl, $S(O)C_{1-4}$alkyl, $SO_2C_{1-4}$alkyl, $O_2CC_{1-4}$alkyl, E, or W—$(CH_2)_l$E;

E represents a 4- to 8-membered hydrocarbon ring or an aromatic ring containing from 0 to 4 heteroatoms;

W represents O, S, NH, or $CH_2$;

l represents 0, 1, 2, 3, or 4;

m represents 0, 1, 2, 3, 4, 5, or 6;

n represents 0, 1, 2, 3, or 4.

In a class of this embodiment, the pharmaceutical composition further comprises a pharmaceutically acceptable carrier, excipient, filler, solvent, diluent, coloring agent, or adhesive. The type and dosage of the above additives depend on an administration mode of the pharmaceutical composition.

An administration mode of the pharmaceutical composition is selected from administration through the gastrointestinal tract, intravenous injection, intraperitoneal injection, dermal injection, intramuscular injection, intranasal administration, intraocular administration, administration by inhalation, rectal administration, reproductive tract administration, percutaneous absorption, or other drug delivery methods.

The diseases or physiological disorders which can be effectively alleviated or treated by decreasing TNFα concentration in patients after administering the pharmaceutical composition comprising a compound of Formula (I) or Formula (II)

include but are not limited inflammatory diseases, infectious diseases, autoimmune diseases or malignant tumor diseases. Specifically, the disease includes but is not limited to septic shock, endotoxic shock, hemodynamic shock, septic syndrome, post ischemic reperfusion injury, malaria, mycobacterial infection, meningitis, psoriasis, congestive heart failure, fibrotic disease, cachexia, transplant immune rejection, cancer, autoimmune disease, opportunistic infection in AIDS, erythema nodosum leprosy, lupus erythematosus, refractory lupus erythematosus, Behcet syndrome, regional ileitis, myelodysplastic syndrome, rheumatoid arthritis (RA), hepatitis, nephritis, rheumatoid spondylitis, multiple myeloma, thyroid tumor, kidney cancer, prostate cancer, lymphoma, leukemia, liver cancer, brain glioma, colorectal cancer, lung cancer, stomach cancer, breast cancer, melanoma, cervical cancer, pancreatic cancer, esophageal cancer, oral cancer, throat cancer, or rhinocarcinoma.

The pharmaceutical composition comprising the compound of Formula (I) or Formula (II) may be used in combination with another pharmaceutically acceptable composition.

DETAILED DESCRIPTION OF THE INVENTION

Pharmacological Research: Effects on the release of TNFα in peripheral blood mononuclear cells (PBMCs) stimulated by lipopolysaccharide (LPS) by compounds of the invention Release of cytokine TNFα by PBMCs in the peripheral blood stimulated by lipid polysaccharide (LPS) was studied in vitro. Experiments of inhibition of TNFα in peripheral blood mononuclear cells (PBMCs) stimulated by lipopolysaccharide (LPS) by the compound of Formula (I) or Formula (II) on the release are described below:

PBMCs collected from blood of at least three volunteers were pretreated with heparin by a gradient separation method, and washed three times with a 1640 culture medium (10% calf serum, 2 mM L-glutamine, 100 mM mercaptoethanol, 50 μg/mL streptomycin, and 50 U/mL penicillin). The obtained PBMCs were then placed into a 24-well cell culture plate and the concentration was adjusted to $1 \times 10^6$ cells/mL with 1640 culture medium. The compounds to be tested were dissolved in dimethylsulfoxide to obtain a solution having a required concentration. The solution was added to the above-mentioned cell culture medium and cultured in an incubator (5% $CO_2$, 90% humidity) for 1 hour. Then, LPS (Sigma) was added until the concentration reached 0.1 μg/mL (except for the control).

After 20 hours incubation, the content of TNFα in the supernatant of the PBMC culture medium was assayed using an ELISA kit (America Genzyme Co) by a standard method. The TNFα inhibition rate was calculated using values measured in the control well (not treated) and the test wells (treated with the compound to be tested). The concentration of compounds giving a 50% TNFα inhibition ($IC_{50}$ value) was calculated using nonlinear regression analysis. Each concentration was determined twice and an average value was reported. Results are listed in Table 1.

TABLE 1

Inhibition of the release of TNFα in peripheral blood mononuclear cells (PBMCs) stimulated by (LPS) (3 μM % inhibition rate) by listed compounds

| Compound | Inhibition Rate (%) |
| --- | --- |
| Thalidomide | 22 |
| Example 1 | 87.6 |

TABLE 1-continued

Inhibition of the release of TNFα in peripheral blood mononuclear cells (PBMCs) stimulated by (LPS) (3 μM % inhibition rate) by listed compounds

| Compound | Inhibition Rate (%) |
| --- | --- |
| Example 15 | 40.9 |
| Example 16 | 38.4 |
| Example 17 | 83.5 |
| Example 18 | 84.1 |
| Example 23 | 95.4 |
| Example 26 | 93.6 |
| Example 29 | 87.6 |
| Example 30 | 91.4 |
| Example 31 | 93.6 |
| Example 38 | 94.9 |
| Example 39 | 93.4 |
| Example 40 | 83.6 |
| Example 41 | 91.2 |
| Example 42 | 94.8 |
| Example 54 | 41.4 |
| Example 55 | 50.2 |
| Example 58 | 20.7 |
| Example 59 | 80 |

ABBREVIATIONS

CDI: carbonyl diimidazole; DCM: dichloromethane; THF: tetrahydrofurane, TFA: trifluoroacetic acid; DMAP: 4-(N,N-dimethylamino)pyridine; TEA: triethylamine; DMF: N,N-dimethylformamide; DMSO: dimethyl sulfoxide; $BOC_2O$: di-tert-butyl dicarbonate; BTOH: 1-hydroxybenzotriazole; DCC: N,N-dicyclohexyl carbodiimide.

Intermediate 1

3,4-dicyanothiophene

To a 2000 mL three-necked flask equipped with a mechanic stirrer, a reflux condenser, and an inert gas duct, 96.8 g of 3,4-dibromothiophene, 104 g of cuprous cyanide, and 100 mL of dry DMF were added. After refluxing for 4 h, the reaction mixture was cooled down to room temperature; and a solution obtained by dissolving 400 g of $FeCl_3.6H_2O$ in 700 mL of hydrochloric acid (1.7 N) was added into the reaction mixture. The resultant mixture was allowed to react for 30 min at 60-70° C. After the reaction mixture was fully cooled, 500 mL of DCM was added. The reaction mixture was divided into 300 mL portions and extracted with DCM (2×300 mL). The DCM layers were combined. The extracts were divided into 600 mL portions, and washed successively with 2×50 mL of 6N hydrochloric acid, water, saturated $Na_2CO_3$ solution, and brine; dried over anhydrous $MgSO_4$, filtered, and evaporated to obtain a yellow solid. The solid was washed with a mixture of ethyl acetate:petroleum ether=1:1, and filtered to obtain a white solid (21 g). $^1H$ NMR ($CDCl_3$): δ 8.07 (s, 2H).

Intermediate 2

Thiophene-3,4-dicarboxylic acid

To a 500 mL round bottom flask equipped with an electro-magnetic stirrer and a reflux condenser, 15.978 g of 3,4-dicyanothiophene, 43.997 g of KOH, and 174 mL of ethylene glycol were added; and the mixture was refluxed for 4 h. After the reaction mixture was cooled, 350 mL of water was added, and the aqueous layer was extracted with ether (2×100 mL).

The ether layer was removed, the aqueous layer was cooled down in an ice bath, and an excess of strong hydrochloric acid was added until a white precipitate was formed. The solid was filtered and dissolved in 2000 mL of ether. The filtrate was extracted with ether (3×300 mL). The organic layers were combined, dried over anhydrous $MgSO_4$, filtered, and evaporated to remove the solvent. 15 g of white solid was obtained and recrystallized from water. $^1H$ NMR (DMSO-$d_6$): δ 10.35 (brs, 2H), 8.17 (s, 2H); MS (m/z): 171 (M−1)$^+$.

Intermediate 3

Thiophene (3,4-c)furyl-1,3-dione

To a 250 mL round bottom flask equipped with an electromagnetic stirrer, a reflux condenser and a drying tube, 15 g of thiophene-3,4-dicarboxylic acid and 120 mL of acetic anhydride were added. The mixture was refluxed for 3 h, and evaporated to remove solvent. 13 g of deep brown solid was obtained.

Intermediate 4

2-nitrothiophene-3,4-dicarboxylic acid

To a 250 mL round bottom flask equipped with an electromagnetic stirrer and a drying tube, 40 mL of fuming nitric acid (95%) was added. The solution was cooled down to a temperature of between 0 and 5° C. 10 g of Intermediate 3 was added in portions (1 g at a time), and then the mixture was allowed to react for 30 min while maintaining the temperature. A yellow solid had precipitated out. The reaction mixture was then poured into 80 g of ice-water mixture, and extracted with ethyl acetate (3×100 mL). The organic layers were combined, washed with water (2×50 mL) and brine, dried over anhydrous $MgSO_4$, filtered, and evaporated to remove the solvent. A yellow solid (10 g) was obtained. MS (m/z): 216 (M−1)$^+$.

Intermediate 5

4-nitrothieno(3,4-c)furan-1,3-dione

To a 250 mL round bottom flask equipped with an electromagnetic stirrer, a reflux condenser and a drying tube, 10 g of Intermediate 4 and 100 mL of acetic anhydride were added. The mixture was stirred for 3 h, and evaporated to remove the solvent. A deep brown solid (9 g) was obtained.

Intermediate 6 methyl
3-amino-3-(3,4-dimethoxy-phenyl)propionate

To a 50 mL round bottom flask equipped with an electromagnetic stirrer and a drying tube, 15 mL of anhydrous methanol was added. The solution was cooled on an ice-sodium chloride bath to minus 10° C., and 2 mL of $SOCl_2$ was added slowly. The reaction mixture was allowed to react for an hour at room temperature. Then 2.25 g of 3-amino-3-(3, 4-dimethoxy-phenyl)-propionic acid (prepared according to a method disclosed in *J. Med. Chem.* 1996, 39, 3238) was added. The reaction mixture was allowed to react for 3 hours at room temperature, and then refluxed for 40 minutes. After the solution was evaporated to remove the solvent, 100 mL of $CHCl_3$ and saturated $NaHCO_3$ were added, and the layers were separated. The organic layer was washed successively with 30 mL of water and saturated brine, dried over anhydrous $MgSO_4$, filtered, evaporated, and purified by column chromatography to give 1.9 g of oil-like products. $^1H$ NMR ($CDCl_3$): δ 6.77-6.88 (m, 3H), 4.34 (t, 1H, J=5 Hz), 3.85 (s, 3H), 3.82 (s, 3H), 3.64 (s, 3H), 2.61 (d, 2H, J=5 Hz), 1.83 (t, 2H, J=6 Hz)

Intermediate 7 methyl
3-amino-3-(3-ethoxy-4-methoxy-phenyl)propionate

The title compound was prepared following the method for preparing Intermediate 6 except that 3-amino-3-(3,4-dimethoxy-phenyl)propionic acid was substituted with 3-amino-3-(3-ethoxy-4-methoxy-phenyl)propionic acid. $^1H$ NMR ($CDCl_3$): δ 6.77-6.86 (m, 3H), 4.30 (s, 1H), 3.85 (t, 2H, J=5 Hz), 3.79 (s, 3H), 3.62 (s, 3H), 2.59 (s, 2H), 1.85 (d, 2H, J=5 Hz), 1.40 (s, 3H).

Intermediate 8 methyl
3-amino-3-(3-propoxy-4-methoxy-phenyl)propionate

The title compound was prepared following the method for preparing Intermediate 6 except that 3-amino-3-(3,4-dimethoxy-phenyl)propionic acid was substituted with 3-amino-3-(-(3-propoxy-4-methoxy-phenyl)propionic acid. $^1H$ NMR ($CDCl_3$): δ 6.78-6.89 (m, 3H), 4.33 (q, 1H, J=5 Hz), 3.95 (t, 2H, J=5 Hz), 3.82 (s, 3H), 3.65 (s, 3H), 2.62 (d, 2H, J=5 Hz), 1.79-1.86 (m, 2H), 1.00 (t, 3H, J=6 Hz).

Intermediate 9 methyl 3-amino-3-(3-isopropoxy-4-methoxy-phenyl)
propionate

The title compound was prepared following the method for preparing Intermediate 6 except that 3-amino-3-(3,4-dimethoxy-phenyl)-propionic acid was substituted with 3-amino-3-(-(3-isopropoxy-4-methoxy-phenyl)propionic acid. $^1H$ NMR ($CDCl_3$): δ 6.76-6.90 (m, 3H), 4.48-4.54 (m, 1H), 4.32 (t, 1H, J=5 Hz), 3.80 (s, 3H), 3.64 (s, 3H), 2.60 (d, 2H, J=5 Hz), 1.79 (s, 2H), 1.32 (d, 6H, J=6 Hz).

Intermediate 10 methyl 3-amino-3-(3-cyclopentyloxy-4-methoxy-phenyl)propionate

The title compound was prepared following the method for preparing Intermediate 6 except that 3-amino-3-(3,4-dimethoxy-phenyl)propionic acid was substituted with 3-amino-3-(3-cyclopentyloxy-4-methoxy-phenyl)propionic acid. $^1H$ NMR ($CDCl_3$): δ 6.78-6.88 (m, 3H), 4.76 (s, 1H), 4.34 (t, 1H, J=5 Hz), 3.80 (s, 3H), 3.66 (s, 3H), 2.62 (d, 2H, J=5 Hz), 1.82-1.92 (m, 8H), 1.58 (s, 2H).

Intermediate 11 methyl
3-amino-3-(3-benzyloxy-4-methoxy-phenyl)propionate

The title compound was prepared following the method for preparing Intermediate 6 except that 3-amino-3-(3,4-dimethoxy-phenyl)propionic acid was substituted with 3-amino-3-(3-benzyloxy-4-methoxy-phenyl)propionic acid. $^1$H NMR (CDCl$_3$): δ 7.26-7.44 (m, 5H), 6.82-6.93 (m, 3H), 5.13 (s, 2H), 4.31 (t, 1H, J=5 Hz), 3.85 (s, 3H), 3.64 (s, 3H), 2.57 (d, 2H, J=5 Hz), 1.80 (d, 2H, J=5 Hz).

Intermediate 12 methyl 3-amino-3-(3-methoxy-4-ethoxy-phenyl)propionate

The title compound was prepared following the method for preparing Intermediate 6 except that 3-amino-3-(3,4-dimethoxy-phenyl)propionic acid was substituted with 3-amino-3-(3-methoxy-4-ethoxy-phenyl)propionic acid. $^1$H NMR (CDCl$_3$): δ 6.79-6.90 (m, 3H), 4.37 (q, 1H, J=5 Hz), 4.06 (q, 2H, J=5 Hz), 3.86 (s, 3H), 3.67 (s, 3H), 2.63 (d, 2H, J=5 Hz), 1.80 (s, 2H), 1.43 (t, 3H, J=5 Hz).

Intermediate 13 methyl 3-amino-3-(3-methoxy-4-propoxy-phenyl)propionate

The title compound was prepared following the method for preparing Intermediate 6 except that 3-amino-3-(3,4-dimethoxy-phenyl)propionic acid was substituted with 3-amino-3-(3-methoxy-4-propoxy-phenyl)propionic acid. $^1$H NMR (CDCl$_3$): δ 6.77-6.86 (m, 3H), 4.32 (q, 1H, J=5 Hz), 3.87-3.95 (m, 2H), 3.80 (s, 3H), 3.61 (s, 3H), 2.62 (d, 2H, J=5 Hz), 1.76 (s, 2H), 0.97 (t, 3H, J=6 Hz).

Intermediate 14 methyl 3-amino-3-(3-methoxy-4-isopropoxy-phenyl)propionate

The title compound was prepared following the method for preparing Intermediate 6 except that 3-amino-3-(3,4-dimethoxy-phenyl)-propionic acid was substituted with 3-amino-3-(3-methoxy-4-isopropoxy-phenyl)propionic acid. $^1$H NMR (CDCl$_3$): δ 6.82-6.89 (m, 3H), 4.44-4.51 (m, 1H), 4.35 (t, 1H, J=5 Hz), 3.83 (s, 3H), 3.66 (s, 3H), 2.62 (d, 2H, J=5 Hz), 1.81 (s, 2H), 1.33 (d, 6H, J=5 Hz).

Intermediate 15 methyl 3-amino-3-(3-methoxy-4-cyclopentyloxy-phenyl)propionate

The title compound was prepared following the method for preparing Intermediate 6 except that 3-amino-3-(3,4-dimethoxy-phenyl)-propionic acid was substituted with 3-amino-3-(3-methoxy-4-cyclopentyloxy-phenyl)propionic acid. $^1$H NMR (CDCl$_3$): δ 6.78-6.88 (m, 3H), 4.69-4.73 (m, 1H), 4.34 (t, 1H, J=5 Hz), 3.82 (s, 3H), 3.66 (s, 3H), 2.62 (d, 2H, J=5 Hz), 1.75-1.92 (m, 8H), 1.58 (s, 2H).

Intermediate 16 methyl 3-amino-3-(3-methoxy-4-benzyloxy-phenyl)propionate

The title compound was prepared following the method for preparing Intermediate 6 except that 3-amino-3-(3,4-dimethoxy-phenyl)propionic acid was substituted with 3-amino-3-(3-methoxy-4-benzyloxy-phenyl)propionic acid. $^1$H NMR (CDCl$_3$): δ 7.26-7.44 (m, 5H), 6.75-6.94 (m, 3H), 5.13 (s, 2H), 4.35 (t, 1H, J=5 Hz), 3.89 (s, 3H), 3.61 (s, 3H), 2.59 (d, 2H, J=5 Hz), 1.84 (d, 2H, J=5 Hz)

Intermediate 17 methyl 3-amino-3-phenyl propionate

The title compound was prepared following the method for preparing Intermediate 6 except that 3-amino-3-(3,4-dimethoxy-phenyl)propionic acid was substituted with 3-amino-3-phenyl-propionic acid. $^1$H NMR (CDCl$_3$): δ 7.23-7.36 (m, 5H), 4.41 (t, 1H, J=5 Hz), 3.67 (s, 3H), 2.66 (d, 2H, J=5 Hz), 1.84 (s, 2H).

Intermediate 18 methyl 3-amino-3-(4-chlorophenyl)propionate

The title compound was prepared following the method for preparing Intermediate 6 except that 3-amino-3-(3,4-dimethoxy-phenyl)-propionic acid was substituted with 3-amino-3-(4-chlorophenyl)propionic acid. $^1$H NMR (CDCl$_3$): δ 7.24-7.32 (m, 5H), 4.38 (t, 1H, J=5 Hz), 3.65 (s, 3H), 2.61 (d, 2H, J=5 Hz), 1.80 (s, 2H).

Intermediate 19 methyl 3-amino-3-(4-benzyloxy phenyl)propionate

The title compound was prepared following the method for preparing Intermediate 6 except that 3-amino-3-(3,4-dimethoxy-phenyl)propionic acid was substituted with 3-amino-3-(4-benzyloxy phenyl)propionic acid.

Intermediate 20 methyl 3-amino propionate

The title compound was prepared following the method for preparing Intermediate 6 except that 3-amino-3-(3,4-dimethoxy-phenyl)propionic acid was substituted with 3-amino propionic acid.

Intermediate 21 methyl 4-amino butyrate

The title compound was prepared following the method for preparing Intermediate 6 except that 3-amino-3-(3,4-dimethoxy-phenyl)-propionic acid was substituted with 4-amino butyric acid.

Intermediate 22

L-methyl 2-amino-2-phenylacetate

The title compound was prepared following the method for preparing Intermediate 6 except that 3-amino-3-(3,4-dimethoxy-phenyl)propionic acid was substituted with L-2-amino-2-phenylacetic acid.

Intermediate 23

D-methyl 2-amino-2-phenylacetate

The title compound was prepared following the method for preparing Intermediate 6 except that 3-amino-3-(3,4-dimethoxy-phenyl)-propionic acid was substituted with D-2-amino-2-phenylacetic acid.

Intermediate 24

L-phenylalanine methyl ester

The title compound was prepared following the method for preparing Intermediate 6 except that 3-amino-3-(3,4-dimethoxy-phenyl)propionic acid was substituted with L-phenylalanine MS (m/z): 180 [M+1]$^+$

Intermediate 25 methyl 3-amino-3-(3-methyl-thiophene-2-yl)propionate 12.6 g of 3-methyl-thiophene-2-carbaldehyde was dissolved in 150 mL of 95% alcohol, and 15.4 g of ammonium acetate was added at 45° C., then 20.8 g of malonate was added. The solution was refluxed for 16 hours, then cooled, and filtered to give a solid of 3-amino-3-(3-methyl-thiophene-2-yl)propionic acid.

To a 50 mL round bottom flask equipped with an electromagnetic stirrer and a drying tube, 15 mL of anhydrous methanol was added. The solution was cooled in an ice water-sodium chloride bath to minus 10° C., and 2 mL of SOCl$_2$ was added slowly. The reaction mixture was allowed to react for an hour at room temperature. Then 1.85 g of 3-amino-3-(3-methyl-thiophene-2-yl)propionic acid was added. The mixture was allowed to react for 3 hours at room temperature, then refluxed for 40 minutes. After the solution was evaporated to remove the solvent, 100 mL of CHCl$_3$ and 100 mL saturated NaHCO$_3$ were added, and the layers were separated. The organic layer was washed successively with 30 mL of water and 30 mL of saturated brine, dried over anhydrous MgSO$_4$, filtered, evaporated, and purified by column chromatography to give an oil-like product. MS (m/z): 200 [M+1]$^+$.

Intermediate 26 ethyl 3-amino-3-(3-ethoxy-4-methoxy-phenyl)propionate

To a 50 mL round bottom flask equipped with an electromagnetic stirrer and a drying tube, 2.39 g of 3-amino-3-(3-ethoxy-4-methoxy-phenyl)propionic acid and 15 mL of anhydrous alcohol were added. The solution was cooled on an sodium chloride-ice water bath to minus 10° C., and 2 mL of SOCl$_2$ was added slowly. The reaction mixture was allowed to react for 3 hours at room temperature, and then refluxed for 40 minutes. After the solution was evaporated to remove the solvent, 100 mL of CHCl$_3$ and saturated NaHCO$_3$ were added, and the layers were separated. The organic layer was washed successively with 30 mL of water and 30 mL of saturated brine, dried over anhydrous MgSO$_4$, filtered, evaporated, and purified by column chromatography to give an oil-like product. MS (m/z): 268 [M+1]$^+$.

Intermediate 27 ethyl 3-amino-3-(3-methoxy-4-ethoxy-phenyl)propionate

The title compound was prepared following the method for preparing Intermediate 26 except that 3-amino-3-(3-ethoxy-4-methoxy-phenyl)propionic acid was substituted with 3-amino-3-(3-methoxy-4-ethoxy-phenyl)propionic acid. MS (m/z): 268 [M+1]$^+$.

Intermediate 28

3-amino-3-(3-methoxy-4-ethoxy-phenyl)propionitrile

To a 50 mL round bottom flask equipped with an electromagnetic stirrer, a reflux condenser and a drying tube, 0.368 g of 3-(1,3-dioxoisoindolyl-2-yl)-3-(3-methoxy-4-ethoxy-phenyl)propionamide (prepared according to a method disclosed in *Bioorg. Med. Chem. Lett.* 1998, 8, 2669), 0.381 g of p-toluenesulfonyl chloride and 5 mL of dried pyridine were added. The solution was allowed to react for 6 hours at 40° C. and then evaporated to remove the solvent. 30 mL of ethyl acetate was added and the resultant solution was washed successively with 10 mL of 2N hydrochloric acid, 20 mL of water and saturated brine, dried over anhydrous MgSO$_4$, filtered, evaporated, and purified by column chromatography to give 0.285 g of 3-(1,3-dioxo-isoindolyl-2-yl)-3-(3-methoxy-4-ethoxy-phenyl)propionitrile as a white solid.

$^1$H NMR (CDCl$_3$): δ 7.85 (q, 2H, J=2 Hz), 7.40 (q, 2H, J=2 Hz), 7.08 (t, 2H, J=2 Hz), 6.83 (d, 1H, J=6 Hz), 5.63 (dd, 1H, J=5 Hz, J=7 Hz), 4.10 (q, 2H, J=6 Hz), 3.85 (s, 3H), 3.84 (dd, 1H, J=7 Hz, J=12 Hz), 3.28 (dd, 1H, J=5 Hz, J=12 Hz), 1.46 (t, 3H, J=5 Hz).

The solid was dissolved in 3 mL of anhydrous methanol and 3 mL of THF, and 12 mL of aqueous methylamine (25-30%) were added. The solution was stirred overnight at room temperature, evaporated to remove methanol and THF, and 20 mL of CHCl$_3$ and 20 mL 2N hydrochloric acid were added. The hydrochloric acid layer was removed. The pH value of the solution was adjusted with 5% sodium hydroxide solution to 8. The solution was extracted with 20 mL of CHCl$_3$ twice, then the organic layers were combined, and washed successively with 20 mL of water and saturated brine, dried over anhydrous MgSO$_4$, filtered, evaporated, and purified by column chromatography to give 0.117 g of the title product as a white solid. $^1$H NMR (CDCl$_3$—CD$_3$OD): δ 6.96 (s, 1H), 6.87 (d, 1H, J=6 Hz), 6.83 (d, 1H, J=6 Hz), 4.71 (t, 1H, J=5 Hz), 4.13 (q, 2H, J=5 Hz), 3.87 (s, 3H), 2.81 (dd, 1H, J=7 Hz, J=12 Hz), 2.67 (dd, 1H, J=5 Hz, J=12 Hz), 1.47 (t, 3H, J=5 Hz); MS (m/z): 221 [M+1]$^+$.

Intermediate 29

3-amino-3-(3,4-dimethoxy-phenyl)propionitrile

The title compound was prepared following the method for preparing Intermediate 28 except that 3-(1,3-dioxo-isoindolyl-2-yl)-3-(3-methoxy-4-ethoxy-phenyl)propionamide was substituted with 3-(1,3-dioxo-isoindolyl-2-yl)-3-(3,4-dimethoxy-phenyl)propionamide.

Intermediate 30

3-amino-3-(3-methoxy-4-benzyloxyphenyl)propionitrile

The title compound was prepared following the method for preparing Intermediate 28 except that 3-(1,3-dioxo-isoindolyl-2-yl)-3-(3-methoxy-4-ethoxy-phenyl)propionamide was substituted with 3-(1,3-dioxo-isoindolyl-2-yl)-3-(3-methoxy-4-benzyloxy-phenyl)propionamide. $^1$H NMR (CDCl$_3$—CD$_3$OD): δ 7.29-7.44 (m, 5H), 6.96 (s, 1H), 6.87 (d, 1H, J=6 Hz), 6.83 (d, 1H, J=6 Hz), 5.14 (s, 2H), 4.26 (t, 1H, J=5 Hz), 3.91 (s, 3H), 2.65-2.73 (m, 2H).

Intermediate 31

3-amino-3-(3-ethoxy-4-methoxy-phenyl)propionitrile

The title compound was prepared following the method for preparing Intermediate 28 except that 3-(1,3-dioxo-isoindolyl-2-yl)-3-(3-methoxy-4-ethoxy-phenyl)propionamide was substituted with 3-(1,3-dioxo-isoindolyl-2-yl)-3-(3-ethoxy-4-methoxy-phenyl)propionamide.

Intermediate 32

3-amino-3-(3-cyclopentyloxy-4-methoxy-phenyl)propionitrile

The title compound was prepared following the method for preparing Intermediate 28 except that 3-(1,3-dioxo-isoindolyl-2-yl)-3-(3-methoxy-4-ethoxy-phenyl)propionamide was substituted with 3-(1,3-dioxo-isoindolyl-2-yl)-3-(3-cyclopentyloxy-4-methoxy-phenyl)propionamide.

Intermediate 33

3-amino-3-(3-methoxy-4-benzyloxyphenyl)propionamide 0.430 g of 3-(1,3-dioxo-isoindolyl-2-yl)-3-(3-methoxy-4-benzyloxy-phenyl)propionamide prepared by a method disclosed in *Bioorg. Med. Chem. Lett.* 1998, 8, 2669) was dissolved in 3 mL of anhydrous methanol and 3 mL of THF, and 15 mL of aqueous methylamine (25-30%) was added. The solution was stirred overnight at room temperature, evaporated to remove methanol and THF, and the residue was extracted twice with 30 mL of CHCl$_3$ each time. The organic layers were combined, washed successively with 20 mL of water and saturated brine, dried over anhydrous MgSO$_4$, filtered, evaporated, and purified by column chromatography to give 0.181 g of white solid. $^1$H NMR (CDCl$_3$—CD$_3$OD): δ 7.31-7.44 (m, 5H), 6.96 (s, 1H), 6.87 (d, 1H, J=6 Hz), 6.82 (d, 1H, J=6 Hz), 5.14 (s, 2H), 4.33-4.35 (m, 1H), 3.91 (s, 3H), 2.48-2.61 (m, 2H); MS (m/z): 301 [M+1]$^+$.

Intermediate 34

3-amino-3-(3-methoxy-4-benzyloxyphenyl)-N-methyl-propionamide

The title compound was prepared following the method for preparing Intermediate 33 except that 3-(1,3-dioxo-isoindolyl-2-yl)-3-(3-methoxy-4-benzyloxy-phenyl)propionamide was substituted with 3-(1,3-dioxo-isoindolyl-2-yl)-3-(3-methoxy-4-benzyloxy-phenyl)-N-methyl-propionamide.

Intermediate 35

3-amino-3-(3-methoxy-4-benzyloxyphenyl)-N-ethyl-propionamide

The title compound was prepared following the method for preparing Intermediate 33 except that 3-(1,3-dioxo-isoin-dolyl-2-yl)-3-(3-methoxy-4-benzyloxy-phenyl)propionamide was substituted with 3-(1,3-dioxo-isoindolyl-2-yl)-3-(3-methoxy-4-benzyloxy-phenyl)-N-ethyl-propionamide.

Intermediate 36

3-amino-3-(3-methoxy-4-benzyloxyphenyl)-N-phenyl-propionamide

The title compound was prepared following the method for preparing Intermediate 33 except that 3-(1,3-dioxo-isoindolyl-2-yl)-3-(3-methoxy-4-benzyloxy-phenyl)propionamide was substituted with 3-(1,3-dioxo-isoindolyl-2-yl)-3-(3-methoxy-4-benzyloxy-phenyl)-N-phenyl-propionamide.

Intermediate 37

3-amino-3-(3-ethoxy-4-methoxyphenyl)-N-benzyl-propionamide

The title compound was prepared following the method for preparing Intermediate 33 except that 3-(1,3-dioxo-isoindolyl-2-yl)-3-(3-methoxy-4-benzyloxy-phenyl)propionamide was substituted with 3-(1,3-dioxo-isoindolyl-2-yl)-3-(3-ethoxy-4-methoxyphenyl)-N-benzyl-propionamide.

Intermediate 38

3-amino-3-(3-methoxy-4-ethoxyphenyl)propan-1-ol

To a 100 mL round bottom flask equipped with an electromagnetic stirrer, 0.253 g of Intermediate 12, 20 mL of THF, 10 mL of water, and 0.114 g of NaBH$_4$ were added. The reaction mixture was stirred overnight at room temperature, and then 0.5N hydrochloric acid was added, and the mixture was stirred for an additional hour. The solution was evaporated to remove THF and the pH value was adjusted to 10. 40 mL of CHCl$_3$ was added. The resultant organic layer was washed successively with 20 mL of water and saturated brine, dried over anhydrous MgSO$_4$, filtered, evaporated, and purified by column chromatography to give a white solid. $^1$H NMR (CDCl$_3$—CD$_3$OD): δ 6.89 (s, 1H), 6.85 (s, 2H), 4.06-4.14 (m, 3H), 3.70-3.80 (m, 1H), 1.87-2.01 (m, 1H), 1.44 (t, 3H, J=5 Hz); MS (m/z): 226 [M+1]$^+$ Intermediate 39

3-amino-3-(3-ethoxy-4-methoxyphenyl)propan-1-ol

The title compound was prepared following the method for preparing Intermediate 38 except that Intermediate 12 was substituted with Intermediate 7.

Intermediate 40

3-(3-methoxy-4-benzyloxyphenyl)-3-(tert-butoxycarbonylamino)propionic acid

To a 250 mL round bottom flask equipped with an electromagnetic stirrer and a drying tube, 6.3 g of Intermediate 16, 50 mL of dry DCM were added. The solution was cooled on an ice bath and 5.23 g of BOC$_2$O was added, and the mixture was stirred overnight at room temperature. 0.5N hydrochloric acid was added to adjust the pH value to 3. 100 mL of DCM was added and the organic layer was washed successively with 50 mL of water and saturated brine, dried over anhydrous MgSO$_4$, filtered, evaporated, and purified by column chromatography to give 3-(3-methoxy-4-benzyloxyphenyl)-3-(tert-butoxycarbonylamino)methyl propionate, as a white solid.

4.15 g of 3-(3-methoxy-4-benzyloxyphenyl)-3-(tert-butoxycarbonylamino)methyl propionate was dissolved in 10 mL of anhydrous methanol and 50 mL of THF, and 20 mL of 1N LiOH solution added. The solution was stirred at room temperature for 2 hours, and 1N hydrochloric acid was added to adjust the pH value to 3. The resultant solution was extracted with 100 mL of $CHCl_3$, and the obtained organic layer was washed successively with 50 mL of water and saturated brine, dried over anhydrous $MgSO_4$, filtered, evaporated, and purified by column chromatography to give 3.414 g of a white solid. $^1H$ NMR ($CDCl_3$): δ 7.29-7.42 (m, 5H), 6.84 (s, 1H), 6.82 (d, 1H, J=6 Hz), 6.82 (d, 1H, J=6 Hz), 5.12 (s, 2H), 3.87 (s, 3H), 2.80-2.90 (m, 2H), 1.41 (s, 9H).

Intermediate 41

3-amino-3-(3-methoxy-4-benzyloxyphenyl)-1-(piperidine-1-yl)propan-1-one

To a 100 mL round bottom flask equipped with an electromagnetic stirrer and a drying tube, 0.401 g of Intermediate 40, 0.149 g of BTOH, 0.1 g of piperidine and 10 mL of dry THF were added. The solution was cooled on an ice bath and 0.227 g of DCC were added. The reaction mixture was stirred overnight at room temperature. Cyclohexyl urea was removed by filtration, and THF was evaporated. Then 70 mL of $CHCl_3$ was added and the organic layer was washed successively with saturated $NaHCO_3$ solution, water and saturated brine, dried over anhydrous $MgSO_4$, filtered, evaporated, and purified by column chromatography to give a white solid.

The solid was dissolved in 6 mL of DCM and 2 mL of TFA, and stirred for 4 hours at room temperature. The solvent was evaporated, and the pH value was adjusted to 9 with 5% NaOH solution. The resultant solution was extracted with 70 mL of $CHCl_3$. The organic layer was washed successively with water and saturated brine, dried over anhydrous $MgSO_4$, filtered, evaporated, and purified by column chromatography to give 0.217 g of white solid. MS (m/z): 369 $[M+1]^+$ Intermediate 42

3-amino-3-(3-methoxy-4-benzyloxyphenyl)-N—N-dimethyl propionamide

The title compound was prepared following the method for preparing Intermediate 41 except that piperidine was substituted with dimethylamine.

Intermediate 43

3-amino-3-(3-methoxy-4-benzyloxyphenyl)-N—N-diethyl propionamide

The title compound was prepared following the method for preparing Intermediate 41 except that piperidine was substituted with diethylamine.

Intermediate 44

3-amino-3-(3-methoxy-4-benzyloxyphenyl)-N-methyl-N-phenyl propionamide

The title compound was prepared following the method for preparing Intermediate 41 except that piperidine was substituted with N-methyl aniline.

Intermediate 45

Tert-butyl 1-(3-methoxy-4-benzyloxyphenyl)-3-hydroxypropyl carbamate

To a 250 mL round bottom flask equipped with an electromagnetic stirrer and a drying tube, 2.6 g of Intermediate 40, 30 mL of dry THF, and 1.68 g of CDI were added. The solution was stirred overnight at room temperature, and then added dropwise to another solution prepared by dissolving 1.73 g of $NaBH_4$ in 20 mL of THF and 30 mL of water. After mixing, the reaction mixture was stirred for an hour, and the pH value was adjusted first to 5 with 1N hydrochloric acid, then to 8 with saturated $Na_2CO_3$ solution. 100 mL of $CHCl_3$ was added and the organic layer was washed successively with water and saturated brine, dried over anhydrous $MgSO_4$, filtered, evaporated, and purified by column chromatography to give 2.25 g of a white solid. $^1H$ NMR ($CDCl_3$): δ 7.22-7.44 (m, 5H), 6.75-6.85 (m, 3H), 5.14 (s, 2H), 4.87-4.92 (m, 1H), 3.87 (s, 3H), 3.67-3.72 (m, 2H), 2.02 (s, 1H), 1.77 (s, 1H), 1.43 (s, 9H).

Intermediate 46

Tert-butyl 1-(3-methoxy-4-benzyloxyphenyl)-3-iodopropyl carbamate

To a 100 mL three-necked flask equipped with an electromagnetic stirrer, a constant pressure funnel, and an inert gas duct, 0.655 g of $Ph_3P$ and 20 mL of dry DCM were added. Ten minutes later, 0.635 g of iodine was added, and after 15 minutes of stirring, 0.193 g of imidazole was added to obtain a mixture. 0.387 g of Intermediate 45 was dissolved in 10 mL of dry DCM, and then the resultant solution was transferred to the constant pressure funnel, added dropwise to the above-mentioned mixture, and refluxed for 3 hours. After the solution was cooled down, the organic layer was washed successively with 5% sodium thiosulfate twice, water and saturated brine, dried over anhydrous $MgSO_4$, filtered, evaporated, and purified by column chromatography to give 0.277 g of white solids.

Intermediate 47

1-(3-methoxy-4-benzyloxyphenyl)-3-dimethyl aminopropyl amine

To a 50 mL round bottom flask equipped with an electromagnetic stirrer and a drying tube, 0.249 g of Intermediate 46, 0.287 g of dimethylamine hydrochloride, 0.956 g of $K_2CO_3$, and 10 mL of dry DMF were added. The solution was stirred overnight at room temperature, and then 50 mL of ethyl acetate and 100 mL of water was added. The organic layer was washed successively with water and saturated brine, dried over anhydrous $MgSO_4$, filtered, evaporated, and purified by column chromatography to give 0.13 g of tert-butyl 1-(3-methoxy-4-benzyloxyphenyl)-3-dimethyl amino propyl carbamate, as a white solid. $^1H$ NMR ($CDCl_3$): δ 7.28-7.46 (m, 5H), 6.75-6.85 (m, 3H), 5.15 (s, 2H), 4.87-4.92 (m, 1H), 3.90 (s, 3H), 2.24-2.37 (m, 8H), 2.02 (s, 1H), 1.77 (s, 1H), 1.43 (s, 9H).

The solid was dissolved in 3 mL of DCM and 1 mL of TFA, and stirred for 4 hours at room temperature. The solvent was evaporated, and the pH value of the solution was adjusted to 9 with 5% NaOH. Then the solution was extracted with 50 mL of CHCl₃, and the resultant organic layer was washed with saturated NaHCO₃ solution, water and saturated brine, dried over anhydrous MgSO₄, filtered, evaporated, and purified by column chromatography to give 0.091 g of white solid.

Intermediate 48

1-(3-methoxy-4-benzyloxyphenyl)-3-diethyl aminopropyl amine

The title compound was prepared following the method for preparing Intermediate 47 except that dimethylamine hydrochloride was substituted with diethylamine.

Intermediate 49

1-(3-methoxy-4-benzyloxyphenyl)-3-(piperidine-1-yl)propan-1-amino

The title compound was prepared following the method for preparing Intermediate 47 except that dimethylamine hydrochloride was substituted with piperidine.

Intermediate 50

Tert-butyl 1-(3-ethoxy-4-methoxyphenyl)-3-hydroxypropyl carbamate 2.39 g of 3-amino-3-(3-ethoxy-4-methoxyphenyl)propionic acid (prepared according to a method disclosed in *J. Med. Chem.* 1996, 39, 3238) and 0.4 g of NaOH solution were dissolved in 20 mL of water, and 10 mL of THF were added. The solution was cooled on an ice bath and 2.616 g of BOC₂O was added, and the reaction mixture was stirred for 3 hours at room temperature. 120 mL of CHCl₃ was added. Then 1N hydrochloric acid was added to adjust the pH value to 2. After the layers were separated, the organic layer was washed successively with water and saturated brine, dried over anhydrous MgSO₄, filtered, evaporated, and purified by column chromatography to give 2.812 g of a white solid. ¹H NMR (CDCl₃): δ 6.82 (t, 3H, J=3 Hz), 5.34 (t, 1H, J=3 Hz), 5.03 (d, 1H, J=3 Hz), 4.09 (q, 2H, J=5 Hz), 3.85 (s, 3H), 2.75-2.98 (m, 2H), 1.46 (s, 9H), 1.43 (s, 3H, J=5 Hz).

The solid was dissolved in 30 mL of dry THF, and 1.62 g of CDI was added. The solution was stirred overnight at room temperature. The resultant solution was added dropwise to another solution prepared by dissolving 1.73 g of NaBH₄ in 20 mL of THF and 30 mL of water. After mixing, the mixture was stirred for an hour. The pH value was adjusted to 5 with 1N hydrochloric acid, then to 8 with saturated Na₂CO₃ solution. 100 mL of CHCl₃ was added and the organic layer was washed successively with water and saturated brine, dried over anhydrous MgSO₄, filtered, evaporated, and purified by column chromatography to give a white solid. ¹H NMR (CDCl₃): δ 6.83 (d, 3H, J=5 Hz), 4.94 (d, 1H, J=6 Hz), 4.82 (s, 1H), 4.10 (q, 2H, J=5 Hz), 3.86 (s, 3H), 3.70 (dd, 2H, J=3 Hz, J=6 Hz), 2.05 (d, 1H, J=6 Hz), 1.81 (dd, 2H, J=6 Hz, J=10 Hz), 1.46 (s, 9H), 1.43 (s, 3H, J=5 Hz).

Intermediate 51

Tert-butyl 1-(3-ethoxy-4-methoxyphenyl)-3-iodpropyl carbamate

The title compound was prepared following the method for preparing Intermediate 46 except that Intermediate 45 was substituted with Intermediate 50.

Intermediate 52

1-(3-ethoxy-4-methoxy-phenyl)-3-methoxy-1-propylamine 0.435 g of Intermediate 51 was dissolved in 10 mL of anhydrous methanol, and then 0.162 g of sodium methoxide and 0.03 g of tetrabutylammonium iodide were added. The solution was refluxed for 6 hours. After cooling, 50 mL of ethyl acetate and 10 mL of water were added. The organic layer was washed successively with water and saturated brine, dried over anhydrous MgSO₄, filtered, and evaporated to give a solid. The solid was dissolved in 63 mL of DCM and 2 mL of TFA, and stirred for 4 hours at room temperature. The solvent was evaporated, and the pH value was adjusted to 9 with 5% NaOH. 50 mL of CHCl₃ was added to extract the solution, and the resultant organic layer was washed successively with saturated NaHCO₃, water and saturated brine, dried over anhydrous MgSO₄, filtered, and evaporated to give a white solid. MS (m/z): 240 [M+1]⁺.

Intermediate 53

4-Tert butoxycarbonyl thiophene 3-carboxylic acid

To a 250 mL round bottom flask equipped with an electromagnetic stirrer and a drying tube, 15.4 g of Intermediate 3, 1.22 g of DMAP, 40 mL of tert-butyl alcohol, 18 mL of dried TEA and 40 mL of DCM were added, stirred overnight at room temperature. The solvent was evaporated, and 200 mL of CHCl₃ and 50 mL of water were added. The organic layer was washed successively with 1N hydrochloric acid, water and saturated brine, dried over anhydrous MgSO₄, filtered, and evaporated to give a solid.

Intermediate 54

Tert-butyl 4-hydroxymethyl-thiophene-3-carboxylate

To a 250 mL round bottom flask equipped with an electromagnetic stirrer and a drying tube, 13.856 g of Intermediate 53, 150 mL of dry THF and 15.552 g of CDI were added, stirred overnight at room temperature. The resultant solution was added dropwise to another solution prepared by dissolving 15.96 g of NaBH₄ in 90 mL of THF and 130 mL of water, and stirred for 30 minutes. 1N hydrochloric acid was added to adjust the pH value to 5. The THF was evaporated, and the solution was extracted with 200 mL of CHCl₃. The organic layer was washed successively with saturated NaHCO₃ solution, 1N hydrochloric acid, water and saturated brine, dried over anhydrous MgSO₄, filtered, evaporated, and purified by column chromatography to give 13.74 g of solid. ¹H NMR (CDCl₃): δ 8.03 (d, 1H, J=3 Hz), 7.17 (d, 1H, J=3 Hz), 4.70 (s, 2H), 1.58 (s, 9H).

Intermediate 55

Tert-butyl 4-iodine methyl thiophene-3-carboxylate

To a 500 mL three-necked flask equipped with an electromagnetic stirrer, a constant pressure funnel, and an inert gas duct, 10.492 g of Ph₃P and 240 mL of dry DCM were added. Ten minutes later, 10.172 g of iodine was added, and it was stirred for 15 minutes. Then, 3.094 g of imidazole was added to obtain a mixture. 3.428 g of Intermediate 54 was dissolved in 80 mL of dry DCM, and the resultant solution was transferred to the constant pressure funnel, added dropwise to the above-mentioned mixture, and refluxed for an hour. After the solution was cooled down, the organic layer was washed successively with 5% sodium thiosulfate twice, water and saturated brine, dried over anhydrous $MgSO_4$, filtered, evaporated, and purified by column chromatography to give 3.556 g of oil-like products.

Intermediate 56

1-(3-ethoxy-4-methoxy-phenyl)-3-methylthio-1-propanamine 0.435 g of Intermediate 51 was dissolved in 10 mL of anhydrous DMF, and 0.210 g of sodium methoxide and 0.03 g of tetrabutylammonium iodide were added. The solution was allowed to react for 4 hours at 70° C. After cooling, 50 mL of ethyl acetate and 30 mL of water were added. The organic layer was washed successively with water and saturated brine, dried over anhydrous $MgSO_4$, filtered, and evaporated to give a solid. The solid was dissolved in 63 mL of DCM and 2 mL of TFA, and stirred for 4 hours at room temperature. The solvent was evaporated, and the pH value was adjusted to 9 with 5% NaOH. 50 mL of $CHCl_3$ was added to extract the solution, and the resultant organic layer was washed successively with saturated $NaHCO_3$, water and saturated brine, dried over anhydrous $MgSO_4$, filtered, evaporated, and purified by column chromatography to give a white solid. MS (m/z): 256 $[M+1]^+$.

Intermediate 57

1-(3-ethoxy-4-methoxy-phenyl)-3-methylsulfinyl-1-propanamine 0.128 g of Intermediate 56 was dissolved in 10 mL of anhydrous methanol, and 0.50 mL of 30% $H_2O_2$ was added. The solution was allowed to react for 4 hours at room temperature. Then 50 mL of ethyl acetate and 30 mL of water were added. The resultant organic layer was washed successively with water and saturated brine, dried over anhydrous $MgSO_4$, filtered, and evaporated to give a white solid. MS (m/z): 272 $[M+1]^+$.

Intermediate 58

3-BOC-amino-3-(3-ethoxy-4-methoxy-phenyl)propan-1-ol

To a 250 mL round bottom flask equipped with an electromagnetic stirrer and a drying tube, 6.3 g of Intermediate 39, 3 mL of TEA, and 50 mL of dry DCM were added. The solution was cooled on an ice bath and 4.53 g of $BOC_2O$ was added. The reaction mixture was stirred overnight at room temperature. 0.5N hydrochloric acid was added to adjust the pH value to 3, and then 100 mL of DCM was added. The organic layer was washed successively with 50 mL of water and saturated brine, dried over anhydrous $MgSO_4$, filtered, and evaporated to give the title compound as a white solid.

Intermediate 59

3-BOC-amino-3-(3-ethoxy-4-methoxy-phenyl)propionaldehyde

To a 250 mL round bottom flask equipped with an electromagnetic stirrer and a drying tube, 3.2 g of Intermediate 58, 5.8 g of $MnO_2$ and 50 mL of dried acetic acid were added. The solution was stirred overnight at room temperature, filtered, and evaporated to remove solvent. Then 100 mL of DCM was added. The organic layer was washed successively with 50 mL of water and saturated brine, dried over anhydrous $MgSO_4$, filtered, and evaporated to give the title compound.

Intermediate 60

3-BOC-amino-3-(3-ethoxy-4-methoxy-phenyl)propionaldehyde oxime methyl ether

To a 100 mL round bottom flask equipped with an electromagnetic stirrer and a drying tube, 1.3 g of Intermediate 59, 0.8 g of $NH_2OMe$ HCl, 2.2 g of $NaHCO_3$ powder, and 50 mL of anhydrous alcohol were added. The solution was stirred and refluxed for 3 hours, filtered, and evaporated to remove solvent. Then 100 mL of DCM was added. The organic layer was washed successively with 50 mL of water and saturated brine, dried over anhydrous $MgSO_4$, filtered, and evaporated to give the title compound.

Intermediate 61

3-Amino-3-(3-ethoxy-4-methoxy-phenyl)propionaldehyde oxime methyl ether

To a 100 mL round bottom flask equipped with an electromagnetic stirrer and a drying tube, 0.5 g of Intermediate 60 and 10 mL of 30% TEA/DCM were added. The solution was stirred for an hour, and evaporated to remove the solvent. Then 30 mL of DCM was added. The organic layer was washed successively with 10 mL of saturated $NaHCO_3$, water, and saturated brine, dried over anhydrous $MgSO_4$, filtered, and evaporated to give the title compound.

Intermediate 62

3-BOC-amino-3-(3-ethoxy-4-methoxy-phenyl)butan-2-ol

To a 50 mL round bottom flask equipped with an electromagnetic stirrer and a nitrogen inlet, 1.6 g of Intermediate 59 and 25 mL of dry THF were added. The solution was cooled on an ice bath and 10 mL of 1M MeMgI/ether were added. After the mixture was stirred for 3 hours, 1N ammonium chloride was added. Then 30 mL of DCM were added, and the mixture was filtered. The organic layer was washed successively with 50 mL of water and saturated brine, dried over anhydrous $MgSO_4$, filtered, and evaporated to give the title compound.

Intermediate 63

3-BOC-amino-3-(3-ethoxy-4-methoxy-phenyl)butan-2-one

The title compound was prepared starting from 3-BOC-amino-3-(3-ethoxy-4-methoxy-phenyl)butan-2-ol following the method for preparing Intermediate 59.

Intermediate 64

3-Amino-3-(3-ethoxy-4-methoxy-phenyl)butan-2-ol

The title compound was prepared starting from 3-BOC-amino-3-(3-ethoxy-4-methoxy-phenyl)butan-2-ol following the method for preparing Intermediate 61.

Intermediate 65

3-Amino-3-(3-ethoxy-4-methoxy-phenyl)butan-2-one trifluoro-acetate

The title compound was prepared starting from 3-BOC-amino-3-(3-ethoxy-4-methoxy-phenyl)butan-2-one following the method for preparing Intermediate 61.

Intermediate 66

3-Amino-3-(4-pyridyl)methyl propionate

The title compound was prepared starting from 3-amino-3-(4-pyridyl)propionic acid following the method for preparing Intermediate 6.

EXAMPLES

Example 1 methyl 3-(3,4-dimethoxy-phenyl)-3-(4,6-dioxo-4H-thiophene[3,4-c]pyrrole-5(6H)-yl)propionate To a 50 mL round bottom flask equipped with an electromagnetic stirrer and a drying tube, 0.12 g of Intermediate 6, 0.077 g of intermediate 3 and 10 mL of dry THF were added. The solution was stirred overnight at room temperature, and then 0.1 g of CDI was added, and the reaction mixture was refluxed for 6 hours. The solvent was evaporated in vacuo. 40 mL of ethyl acetate was added, and the obtained organic layer was washed successively with saturated $NaHCO_3$, water, 1N hydrochloric acid, water and saturated brine, dried over anhydrous $MgSO_4$, filtered, and evaporated to give 0.142 g of a solid. $^1$H NMR ($CDCl_3$): δ 7.78 (s, 2H), 7.10 (s, 1H), 7.08 (t, 1H, J=2 Hz), 6.80 (t, 1H, J=3 Hz), 5.70 (dd, 1H, J=5 Hz, J=8 Hz), 3.87 (s, 3H), 3.84 (s, 3H), 3.73 (dd, 1H, J=8 Hz, J=12 Hz), 3.64 (s, 3H), 3.22 (dd, 1H, J=5 Hz, J=12 Hz).

Example 2 methyl 3-(3-Ethoxy-4-methoxy-phenyl)-3-(4,6-dioxo-4H-thiophene[3,4-c]pyrrole-5(6H)-yl)propionate The title compound was prepared following the method of Example 1 except that Intermediate 6 was substituted with Intermediate 7. $^1$H NMR ($CDCl_3$): δ 7.77 (s, 2H), 7.09 (s, 1H), 7.06 (d, 1H, J=6 Hz), 6.79 (t, 1H, J=6 Hz), 5.68 (dd, 1H, J=6 Hz, J=8 Hz), 4.08 (q, 2H, J=5 Hz), 3.82 (s, 3H), 3.72 (dd, 1H, J=8 Hz, J=12 Hz), 3.63 (s, 3H), 3.21 (dd, 1H, J=6 Hz, J=12 Hz), 1.44 (t, 3H, J=5 Hz).

Example 3 methyl 3-(3-Propoxy-4-methoxy-phenyl)-3-(4,6-dioxo-4H-thiophene[3,4-c]pyrrole-5(6H)-yl)propionate The title compound was prepared following the method of Example 1 except that Intermediate 6 was substituted with Intermediate 8. $^1$H NMR ($CDCl_3$): δ 7.76 (s, 2H), 7.07 (s, 1H), 7.05 (d, 1H, J=6 Hz), 6.79 (t, 1H, J=6 Hz), 5.68 (dd, 1H, J=6 Hz, J=8 Hz), 3.96 (t, 2H, J=5 Hz), 3.81 (s, 3H), 3.72 (dd, 1H, J=8 Hz, J=12 Hz), 3.63 (s, 3H), 3.22 (dd, 1H, J=6 Hz, J=12 Hz), 1.81-1.86 (m, 2H), 1.02 (t, 3H, J=5 Hz).

Example 4 methyl 3-(3-Isopropoxy-4-methoxy-phenyl)-3-(4,6-dioxo-4H-thiophene[3,4-c]pyrrole-5(6H)-yl)propionate The title compound was prepared following the method of Example 1 except that Intermediate 6 was substituted with Intermediate 9. $^1$H NMR ($CDCl_3$): δ 7.77 (s, 2H), 7.11 (s, 1H), 7.05 (d, 1H, J=5 Hz), 6.80 (t, 1H, J=6 Hz), 5.68 (dd, 1H, J=5 Hz, J=8 Hz), 4.48-4.57 (m, 1H), 3.83 (s, 3H), 3.72 (dd, 1H, J=8 Hz, J=12 Hz), 3.63 (s, 3H), 3.18 (dd, 1H, J=5 Hz, J=12 Hz), 1.35 (d, 6H, J=5 Hz).

Example 5 methyl 3-(3-Cyclopentyloxy-4-methoxy-phenyl)-3-(4,6-dioxo-4H-thiophene[3,4-c]pyrrole-5(6H)-yl)propionate The title compound was prepared following the method of Example 1 except that Intermediate 6 was substituted with Intermediate 10. $^1$H NMR ($CDCl_3$): δ 7.77 (s, 2H), 7.10 (s, 1H), 7.03 (d, 1H, J=6 Hz), 6.78 (t, 1H, J=6 Hz), 5.68 (dd, 1H, J=5 Hz, J=8 Hz), 4.73-4.77 (m, 1H), 3.79 (s, 3H), 3.72 (dd, 1H, J=8 Hz, J=12 Hz), 3.63 (s, 3H), 3.19 (dd, 1H, J=5 Hz, J=12 Hz), 1.51-1.97 (m, 8H).

Example 6 methyl 3-(3-Benzyloxy-4-methoxy-phenyl)-3-(4,6-dioxo-4H-thiophene[3,4-c]pyrrole-5(6H)-yl)propionate The title compound was prepared following the method of Example 1 except that Intermediate 6 was substituted with Intermediate 11. $^1$H NMR ($CDCl_3$): δ 7.76 (s, 2H), 7.21-7.43 (m, 5H), 7.09 (s, 1H), 7.06 (d, 1H, J=6 Hz), 6.81 (t, 1H, J=6 Hz), 5.63 (dd, 1H, J=5 Hz, J=8 Hz), 5.13 (s, 2H), 3.84 (s, 3H), 3.66 (dd, 1H, J=8 Hz, J=12 Hz), 3.61 (s, 3H), 3.15 (dd, 1H, J=5 Hz, J=12 Hz).

Example 7 methyl 3-(3-Methoxy-4-ethoxy-phenyl)-3-(4,6-dioxo-4H-thiophene[3,4-c]pyrrole-5(6H)-yl)propionate The title compound was prepared following the method of Example 1 except that Intermediate 6 was substituted with Intermediate 12. $^1$H NMR ($CDCl_3$): δ 7.77 (s, 2H), 7.07 (s, 1H), 7.05 (d, 1H, J=6 Hz), 6.79 (t, 1H, J=6 Hz), 5.68 (dd, 1H, J=5 Hz, J=8 Hz), 4.05 (q, 2H, J=5 Hz), 3.85 (s, 3H), 3.71 (dd, 1H, J=8 Hz, J=12 Hz), 3.63 (s, 3H), 3.20 (dd, 1H, J=5 Hz, J=12 Hz), 1.42 (t, 3H, J=5 Hz).

Example 8 methyl 3-(3-Methoxy-4-propoxy-phenyl)-3-(4,6-dioxo-4H-thiophene[3,4-c]pyrrole-5(6H)-yl)propionate The title compound was prepared following the method of Example 1 except that Intermediate 6 was substituted with Intermediate 13. $^1$H NMR ($CDCl_3$): δ 7.77 (s, 2H), 7.07 (s, 1H), 7.05 (d, 1H, J=6 Hz), 6.79 (d, 1H, J=6 Hz), 5.68 (dd, 1H, J=5 Hz, J=8 Hz), 3.93 (t, 2H, J=5 Hz), 3.85 (s, 3H), 3.74 (dd, 1H, J=8 Hz, J=12 Hz), 3.64 (s, 3H), 3.21 (dd, 1H, J=5 Hz, J=12 Hz), 1.81-1.86 (m, 2H), 1.00 (t, 3H, J=5 Hz).

Example 9 methyl 3-(3-Methoxy-4-isopropoxy-phenyl)-3-(4,6-dioxo-4H-thiophene[3,4-c]pyrrole-5(6H)-yl)propionate The title compound was prepared following the method of Example 1 except that Intermediate 6 was substituted with Intermediate 14. $^1$H NMR (CDCl$_3$): δ 7.77 (s, 2H), 7.07 (s, 1H), 7.04 (d, 1H, J=6 Hz), 6.80 (d, 1H, J=6 Hz), 5.68 (dd, 1H, J=5 Hz, J=8 Hz), 4.44-4.53 (m, 1H), 3.83 (s, 3H), 3.75 (dd, 1H, J=8 Hz, J=12 Hz), 3.63 (s, 3H), 3.18 (dd, 1H, J=5 Hz, J=12 Hz), 1.33 (d, 6H, J=5 Hz).

Example 10 methyl 3-(3-Methoxy-4-cyclopentyloxy-phenyl)-3-(4,6-dioxo-4H-thiophene[3,4-c]pyrrole-5(6H)-yl)propionate The title compound was prepared following the method of Example 1 except that Intermediate 6 was substituted with Intermediate 15. $^1$H NMR (CDCl$_3$): δ 7.77 (s, 2H), 7.06 (s, 1H), 7.04 (d, 1H, J=6 Hz), 6.79 (t, 1H, J=6 Hz), 5.68 (dd, 1H, J=5 Hz, J=8 Hz), 4.69-4.72 (m, 1H), 3.83 (s, 3H), 3.74 (dd, 1H, J=8 Hz, J=12 Hz), 3.63 (s, 3H), 3.19 (dd, 1H, J=5 Hz, J=12 Hz), 1.55-1.91 (m, 8H).

Example 11 methyl 3-(3-Methoxy-4-benzyloxy-phenyl)-3-(4,6-dioxo-4H-thiophene[3,4-c]pyrrole-5(6H)-yl)propionate The title compound was prepared following the method of Example 1 except that Intermediate 6 was substituted with Intermediate 16. $^1$H NMR (CDCl$_3$): δ 7.77 (s, 2H), 7.26-7.41 (m, 5H), 7.10 (s, 1H), 7.02 (d, 1H, J=6 Hz), 6.80 (t, 1H, J=6 Hz), 5.68 (dd, 1H, J=5 Hz, J=8 Hz), 5.12 (s, 2H), 3.88 (s, 3H), 3.73 (dd, 1H, J=8 Hz, J=12 Hz), 3.63 (s, 3H), 3.19 (dd, 1H, J=5 Hz, J=12 Hz)

Example 12 methyl 3-(4,6-Dioxo-4H-thiophene[3,4-c]pyrrole-5(6H)-yl)-3-phenylpropionate

The title compound was prepared following the method of Example 1 except that Intermediate 6 was substituted with Intermediate 17. $^1$H NMR (CDCl$_3$): δ 7.79 (s, 2H), 7.51 (d, 2H, J=5 Hz), 7.26-7.35 (m, 3H), 5.78 (dd, 1H, J=4 Hz, J=8 Hz), 3.75 (dd, 1H, J=8 Hz, J=12 Hz), 3.65 (s, 3H), 3.23 (dd, 1H, J=4 Hz, J=12 Hz).

Example 13 methyl 3-(4-Chlorophenyl)-3-(4,6-dioxo-4H-thiophene[3,4-c]pyrrole-5(6H)-yl)propionate The title compound was prepared following the method of Example 1 except that Intermediate 6 was substituted with Intermediate 18. $^1$H NMR (CDCl$_3$): δ 7.78 (s, 2H), 7.44 (d, 2H, J=6 Hz), 7.28 (d, 2H, J=6 Hz), 5.72 (dd, 1H, J=5 Hz, J=7 Hz), 3.66 (dd, 1H, J=7 Hz, J=12 Hz), 3.63 (s, 3H), 3.23 (dd, 1H, J=5 Hz, J=12 Hz).

Example 14 methyl 3-(4-Benzyloxy phenyl)-3-(4,6-dioxo-4H-thiophene[3,4-c]pyrrole-5(6H)-yl)propionate The title compound was prepared following the method of Example 1 except that Intermediate 6 was substituted with Intermediate 19. $^1$H NMR (CDCl$_3$): δ 7.76 (s, 2H), 7.26-7.46 (m, 7H), 7.02 (d, 2H, J=6 Hz), 5.72 (dd, 1H, J=5 Hz, J=8 Hz), 5.02 (s, 2H), 3.72 (dd, 1H, J=8 Hz, J=12 Hz), 3.63 (s, 3H), 3.21 (dd, 1H, J=5 Hz, J=12 Hz).

Example 15 methyl 3-(4,6-Dioxo-4H-thiophene[3,4-c]pyrrole-5(6H)-yl)propionate

The title compound was prepared following the method of Example 1 except that Intermediate 6 was substituted with Intermediate 20. $^1$H NMR (CDCl$_3$): δ 7.84 (s, 2H), 3.94 (d, 2H, J=3 Hz), 3.69 (s, 3H), 2.71 (d, 2H, J=3 Hz).

Example 16 methyl 4-(4,6-Dioxo-4H-thiophene[3,4-c]pyrrole-5(6H)-yl)butyrate

The title compound was prepared following the method of Example 1 except that Intermediate 6 was substituted with Intermediate 21. $^1$H NMR (CDCl$_3$): δ 7.83 (s, 2H), 3.70 (s, 2H), 3.66 (s, 3H), 2.38 (d, 2H, J=3 Hz), 2.01 (d, 2H, J=3 Hz).

Example 17

L-methyl 2-(4,6-dioxo-4H-thiophene[3,4-c]pyrrole-5(6H)-yl)-2-phenylacetate

The title compound was prepared following the method of Example 1 except that Intermediate 6 was substituted with Intermediate 22. $^1$H NMR (CDCl$_3$): δ 7.84 (s, 2H), 7.32-7.53 (m, 5H), 5.94 (s, 1H), 3.81 (s, 3H).

Example 18

D-methyl 2-(4,6-dioxo-4H-thiophene[3,4-c]pyrrole-5(6H)-yl)-2-phenylacetate

The title compound was prepared following the method of Example 1 except that Intermediate 6 was substituted with Intermediate 23. $^1$H NMR (CDCl$_3$): δ 7.84 (s, 2H), 7.32-7.53 (m, 5H), 5.94 (s, 1H), 3.81 (s, 3H).

Example 19

L-methyl 2-(4,6-dioxo-4H-thiophene[3,4-c]pyrrole-5(6H)-yl)-3-phenylpropionate

The title compound was prepared following the method of Example 1 except that Intermediate 6 was substituted with Intermediate 24. MS (m/z): 316 [M+1]$^+$.

Example 20 methyl 3-(3-Methyl-thiophene-2-yl)-3-(4,6-dioxo-4H-thiophene[3,4-c]pyrrole-5(6H)-yl)propionate The title compound was prepared following the method of Example 1 except that Intermediate 6 was substituted with Intermediate 25. MS (m/z): 336 [M+1]$^+$.

Example 21 ethyl 3-(3-ethoxy-4-methoxy-phenyl)-3-(4,6-dioxo-4H-thiophene[3,4-c]pyrrole-5(6H)-yl)propionate The title compound was prepared following the method of Example 1 except that Intermediate 6 was substituted with Intermediate 26. $^1$H NMR (CDCl$_3$): δ 7.78 (s, 2H), 7.11 (s, 1H), 7.08 (d, 1H, J=6 Hz), 6.81 (d, 1H, J=6 Hz), 5.69 (dd, 1H, J=5 Hz, J=8 Hz), 4.07-4.13 (m, 4H), 3.84 (s, 3H), 3.72 (dd, 1H, J=8 Hz, J=12 Hz), 3.20 (dd, 1H, J=5 Hz, J=12 Hz), 1.46 (t, 3H, J=5 Hz), 1.17 (t, 3H, J=5 Hz).

Example 22 ethyl 3-(3-methoxy-4-ethoxy-phenyl)-3-(4,6-dioxo-4H-thiophene[3,4-c]pyrrole-5(6H)-yl)propionate The title compound was prepared following the method of Example 1 except that Intermediate 6 was substituted with Intermediate 27. $^1$H NMR (CDCl$_3$): δ 7.78 (s, 2H), 7.09 (s, 1H), 7.07 (d, 1H, J=6 Hz), 6.81 (d, 1H, J=6 Hz), 5.69 (dd, 1H, J=4 Hz, J=8 Hz), 4.04-4.12 (m, 4H), 3.87 (s, 3H), 3.73 (dd, 1H, J=8 Hz, J=12 Hz), 3.20 (dd, 1H, J=4 Hz, J=12 Hz), 1.44 (t, 3H, J=5 Hz), 1.17 (t, 3H, J=5 Hz)

Example 23 methyl 3-(3,4-Dimethoxy-phenyl)-3-(1-amino-4,6-dioxo-4H-thiophene[3,4-c]pyrrole-5(6H)-yl)propionate To a 50 mL round bottom flask equipped with an electromagnetic stirrer and a drying tube, 0.239 g of Intermediate 6, 0.199 g of intermediate 5 and 10 mL of dry THF were added. The solution was stirred overnight at room temperature, and then 0.26 g of CDI was added, and it was refluxed for 3 hours. The solution was evaporated to remove the solvent. 50 mL of ethyl acetate was added, and the obtained organic layer was washed successively with saturated NaHCO$_3$, water, 1N hydrochloric acid, water, and saturated brine, dried over anhydrous MgSO$_4$, filtered, and evaporated to give 0.379 g of 3-(3,4-dimethoxy-phenyl)-3-(1-nitro-4,6-dioxo-4H-thiophene[3,4-c]pyrrole-5(6H)-yl)methyl propionate, as a solid. The solid was dissolved in 10 mL of acetone, and 0.781 g of sodium hydrosulfite (Na$_2$S$_2$O$_4$) and 10 mL of water were added. The reaction mixture was refluxed for 10 minutes. After the solution was cooled, 20 mL of water added, and the mixture was extracted three times, each time with 20 mL of ethyl acetate. The organic layers were combined, washed successively with water and saturated brine, dried over anhydrous MgSO$_4$, filtered, evaporated, and purified by column chromatography to give 0.079 g of a yellow solid.
$^1$H NMR (CDCl$_3$): δ 7.08 (s, 1H), 7.07 (s, 1H), 6.85 (s, 1H), 6.81 (d, 1H, J=6 Hz), 5.65 (dd, 1H, J=5 Hz, J=8 Hz), 5.30 (brs, 2H), 3.87 (s, 3H), 3.85 (s, 3H), 3.72 (dd, 1H, J=8 Hz, J=12 Hz), 3.66 (s, 3H), 3.21 (dd, 1H, J=5 Hz, J=12 Hz).

Example 24 methyl 3-(3-Ethoxy-4-methoxy-phenyl)-3-(1-amino-4,6-dioxo-4H-thiophene[3,4-c]pyrrole-5(6H)-yl)propionate The title compound was prepared following the method of Example 23 except that Intermediate 6 was substituted with Intermediate 7. $^1$H NMR (CDCl$_3$): δ 7.08 (s, 1H), 7.05 (s, 1H), 6.85 (s, 1H), 6.81 (d, 1H, J=6 Hz), 5.63 (dd, 1H, J=5 Hz, J=8 Hz), 5.23 (brs, 2H), 4.10 (q, 2H, J=5 Hz), 3.84 (s, 3H), 3.70 (dd, 1H, J=8 Hz, J=12 Hz), 3.64 (s, 3H), 3.20 (dd, 1H, J=5 Hz, J=12 Hz), 1.45 (t, 3H, J=5 Hz).

Example 25 methyl 3-(3-Cyclopentyloxy-4-methoxy-phenyl)-3-(1-amino-4,6-dioxo-4H-thiophene[3,4-c]pyrrole-5(6H)-yl)propionate The title compound was prepared following the method of Example 23 except that Intermediate 6 was substituted with Intermediate 10. $^1$H NMR (CDCl$_3$): δ 7.09 (s, 1H), 7.03 (s, 1H), 6.85 (s, 1H), 6.79 (d, 1H, J=6 Hz), 5.63 (dd, 1H, J=5 Hz, J=8 Hz), 5.22 (brs, 2H), 4.75-4.79 (m, 1H), 3.81 (s, 3H), 3.72 (dd, 1H, J=8 Hz, J=12 Hz), 3.66 (s, 3H), 3.19 (dd, 1H, J=5 Hz, J=12 Hz), 1.58-1.96 (m, 8H).

Example 26 methyl 3-(3-Methoxy-4-ethoxy-phenyl)-3-(1-amino-4,6-dioxo-4H-thiophene[3,4-c]pyrrole-5(6H)-yl)propionate The title compound was prepared following the method of Example 23 except that Intermediate 6 was substituted with Intermediate 12. $^1$H NMR (CDCl$_3$): δ 7.05 (s, 1H), 7.02 (s, 1H), 6.83 (s, 1H), 6.78 (d, 1H, J=6 Hz), 5.63 (dd, 1H, J=5 Hz, J=8 Hz), 5.23 (brs, 2H), 4.05 (q, 2H, J=5 Hz), 3.86 (s, 3H), 3.71 (dd, 1H, J=8 Hz, J=12 Hz), 3.67 (s, 3H), 3.18 (dd, 1H, J=5 Hz, J=12 Hz), 1.42 (t, 3H, J=5 Hz).

Example 27 methyl 3-(3-Methoxy-4-propoxy-phenyl)-3-(1-amino-4,6-dioxo-4H-thiophene[3,4-c]pyrrole-5(6H)-yl)propionate The title compound was prepared following the method of Example 23 except that Intermediate 6 was substituted with Intermediate 13. $^1$H NMR (CDCl$_3$): δ 7.06 (s, 1H), 7.05 (s, 1H), 6.84 (s, 1H), 6.79 (d, 1H, J=6 Hz), 5.63 (dd, 1H, J=5 Hz, J=7 Hz), 5.21 (brs, 2H), 3.93 (t, 2H, J=5 Hz), 3.85 (s, 3H), 3.73 (dd, 1H, J=7 Hz, J=12 Hz), 3.65 (s, 3H), 3.18 (dd, 1H, J=5 Hz, J=12 Hz), 1.81-1.86 (m, 2H), 1.00 (t, 3H, J=5 Hz).

Example 28 methyl 3-(3-Methoxy-4-benzyloxy-phenyl)-3-(1-amino-4,6-dioxo-4H-thiophene[3,4-c]pyrrole-5(6H)-yl)propionate The title compound was prepared following the method of Example 23 except that Intermediate 6 was substituted with Intermediate 16. $^1$H NMR (CDCl$_3$): δ 7.28-7.41 (m, 5H), 7.08 (s, 1H), 6.98 (s, 1H), 6.84 (s, 1H), 6.79 (d, 1H, J=6 Hz), 5.62

(dd, 1H, J=4 Hz, J=7 Hz), 5.12 (s, 2H), 3.88 (s, 3H), 3.71 (dd, 1H, J=7 Hz, J=12 Hz), 3.64 (s, 3H), 3.17 (dd, 1H, J=4 Hz, J=12 Hz).

Example 29

L-methyl 2-(1-amino-4,6-dioxo-4H-thiophene[3,4-c]pyrrole-5(6H)-yl)-2-phenylacetate The title compound was prepared following the method of Example 23 except that Intermediate 6 was substituted with Intermediate 22. $^1$H NMR (CDCl$_3$—CD$_3$OD): δ 7.34-7.50 (m, 5H), 6.92 (s, 1H), 5.87 (s, 1H), 3.80 (s, 3H).

Example 30

D-methyl 2-(1-amino-4,6-dioxo-4H-thiophene[3,4-c]pyrrole-5(6H)-yl)-2-phenylacetate The title compound was prepared following the method of Example 23 except that Intermediate 6 was substituted with Intermediate 23. $^1$H NMR (CDCl$_3$—CD$_3$OD): δ 7.33-7.50 (m, 5H), 6.93 (s, 1H), 5.86 (s, 1H), 3.80 (s, 3H)

Example 31 methyl 3-(3-Cyclopentyloxy-4-methoxy-phenyl)-3-(1-acetylamino-4,6-dioxo-4H-thiophene[3,4-c]pyrrole-5(6H)-yl)propionate To a 25 mL round bottom flask equipped with an electromagnetic stirrer and a drying tube, 0.047 g of 3-(3-cyclopentyloxy-4-methoxy-phenyl)-3-(1-amino-4,6-dioxo-4H-thiophene[3,4-c]pyrrole-5(6H)-yl)methyl propionate, 0.03 g of DMAP, and 3 mL of acetic anhydride were added. The solution was stirred at 40° C. for 3 hours, evaporated to remove solvent, and purified by column chromatography to give a white solid. $^1$H NMR (CDCl$_3$): δ 8.88 (s, 1H), 7.27 (d, 1H, J=5 Hz), 7.06 (s, 1H), 7.02 (d, 1H, J=5 Hz), 6.90 (d, 1H, J=6 Hz), 5.64 (dd, 1H, J=5 Hz, J=8 Hz), 4.74-4.77 (m, 1H), 3.81 (s, 3H), 3.75 (dd, 1H, J=8 Hz, J=12 Hz), 3.65 (s, 3H), 3.16 (dd, 1H, J=5 Hz, J=12 Hz), 1.58-1.97 (m, 8H); MS (m/z): 487 [M+1]$^+$.

Example 32 methyl 3-(3-Cyclopentyloxy-4-methoxy-phenyl)-3-(1-methylamino-4,6-dioxo-4H-thiophene[3,4-c]pyrrole-5(6H)-yl)propionate To a 50 mL round bottom flask equipped with an electromagnetic stirrer, 0.089 g of 3-(3-cyclopentyloxy-4-methoxyphenyl)-3-(1-amino-4,6-dioxo-4H-thiophene[3,4-c]pyrrole-5(6H)-yl)methyl propionate, 0.5 mL of iodomethane, 5 mL of anhydrous methanol, and 5 mL of acetone were added. The solution was stirred at 60° C. for 48 hours, evaporated to remove solvent, and purified by column chromatography to give a white solid. MS (m/z): 457 [M−1]$^+$.

Example 33

3-(3-Methoxy-4-ethoxy-phenyl)-3-(4,6-dioxo-4H-thiophene[3,4-c]pyrrole-5(6H)-yl)propionitrile To a 50 mL round bottom flask equipped with an electromagnetic stirrer and a drying tube, 0.066 g of Intermediate 28, 0.046 g of Intermediate 3 and 10 mL of dry THF were added. The solution was stirred overnight at room temperature, and 0.06 g of CDI was added. The reaction mixture was refluxed for 6 hours. Then, the solvent was evaporated and 40 mL of ethyl acetate was added. The resultant organic layer was washed successively with saturated NaHCO$_3$, water, 1N hydrochloric acid and saturated brine, dried over anhydrous MgSO$_4$, filtered, evaporated, and purified by column chromatography to give 0.07 g of a white solid. $^1$H NMR (CDCl$_3$): δ 7.85 (s, 2H), 7.06 (s, 1H), 7.04 (d, 1H, J=6 Hz), 6.83 (d, 1H, J=6 Hz), 5.56 (dd, 1H, J=5 Hz, J=8 Hz), 4.09 (q, 2H, J=5 Hz), 3.85 (s, 3H), 3.81 (dd, 1H, J=8 Hz, J=12 Hz), 3.25 (dd, 1H, J=5 Hz, J=12 Hz), 1.46 (t, 3H, J=5 Hz.

Example 34

3-(3,4-Dimethoxy-phenyl)-3-(4,6-dioxo-4H-thiophene[3,4-c]pyrrole-5(6H)-yl)propionitrile The title compound was prepared following the method of Example 33 except that Intermediate 28 was substituted with Intermediate 29. $^1$H NMR (CDCl$_3$): δ 7.85 (s, 2H), 7.04-7.08 (m, 2H), 6.83 (t, 1H, J=6 Hz), 5.57 (dd, 1H, J=5 Hz, J=8 Hz), 3.88 (s, 3H), 3.85 (s, 3H), 3.80 (dd, 1H, J=8 Hz, J=12 Hz), 3.26 (dd, 1H, J=5 Hz, J=12 Hz).

Example 35

3-(3-Methoxy-4-benzyloxy phenyl)-3-(4,6-dioxo-4H-thiophene[3,4-c]pyrrole-5(6H)-yl)propionitrile The title compound was prepared following the method of Example 33 except that Intermediate 28 was substituted with Intermediate 30. $^1$H NMR (CDCl$_3$): δ 7.84 (s, 2H), 7.26-7.41 (m, 5H), 7.05 (s, 1H), 6.98 (d, 1H, J=6 Hz), 6.82 (t, 1H, J=6 Hz), 5.54 (dd, 1H, J=5 Hz, J=8 Hz), 5.13 (s, 2H), 3.88 (s, 3H), 3.79 (dd, 1H, J=8 Hz, J=12 Hz), 3.22 (dd, 1H, J=5 Hz, J=12 Hz); MS (m/z): 441 [M+Na]$^+$.

Example 36

3-(3-Ethoxy-4-methoxy phenyl)-3-(4,6-dioxo-4H-thiophene[3,4-c]pyrrole-5(6H)-yl)propionitrile The title compound was prepared following the method of Example 33 except that Intermediate 28 was substituted with Intermediate 31. $^1$H NMR (CDCl$_3$): δ 7.84 (s, 2H), 7.05 (s, 1H), 7.03 (s, 1H), 6.82 (d, 1H, J=6 Hz), 5.55 (dd, 1H, J=5 Hz, J=8 Hz), 4.09 (q, 2H, J=5 Hz), 3.84 (s, 3H), 3.80 (dd, 1H, J=8 Hz, J=12 Hz), 3.25 (dd, 1H, J=5 Hz, J=12 Hz), 1.45 (t, 3H, J=5 Hz).

Example 37

3-(3-Cyclopentyloxy-4-methoxy phenyl)-3-(4,6-dioxo-4H-thiophene[3,4-c]pyrrole-5(6H)-yl)propionitrile The title compound was prepared following the method of Example 33 except that Intermediate 28 was substituted with Intermediate 32. $^1$H NMR (CDCl$_3$): δ 7.86 (s, 2H), 7.07 (s, 1H), 7.03 (d, 1H, J=6 Hz), 6.81 (t, 1H, J=6 Hz), 5.56 (dd, 1H, J=5 Hz, J=8 Hz), 4.74-4.78 (m, 1H), 3.82 (s, 3H), 3.81 (dd, 1H, J=8 Hz, J=12 Hz), 3.24 (dd, 1H, J=5 Hz, J=12 Hz), 1.60-1.99 (m, 8H).

Example 38

3-(3-Methoxy-4-ethoxy-phenyl)-3-(1-amino-4,6-dioxo-4H-thiophene[3,4-c]pyrrole-5(6H)-yl)propionitrile To a 50 mL round bottom flask equipped with an electromagnetic stirrer and a drying tube, 0.264 g of Intermediate 28, 0.239 g of Intermediate 5, and 10 mL of dry THF were added. The solution was stirred overnight at room temperature, and 0.3126 g of CDI was added, and it was refluxed for 6 hours. Then, the solvent was evaporated and 50 mL of ethyl acetate was added. The resultant organic layer was washed successively with saturated $NaHCO_3$, water, 1N hydrochloric acid, and saturated brine, dried over anhydrous $MgSO_4$, filtered, and evaporated to give 0.415 g of 3-(3-methoxy-4-ethoxyphenyl)-3-(1-nitro-4,6-dioxo-4H-thiophene[3,4-c]pyrrole-5(6H)-yl)propionitrile.

The solid was dissolved in 10 mL of acetone, and 0.901 g of sodium hydrosulfite ($Na_2S_2O_4$), and 10 mL of water were added. The reaction mixture was refluxed for 10 minutes. After the solution was cooled, 20 mL of water were added, and the mixture was extracted three times, each time with 20 mL ethyl acetate. The organic layers were combined, washed successively with water and saturated brine, dried over anhydrous $MgSO_4$, filtered, evaporated, and purified by column chromatography to give 0.129 g of a yellow solid. $^1H$ NMR ($CDCl_3$): δ 7.04 (s, 1H), 7.02 (d, 1H, J=5 Hz), 6.91 (s, 1H), 6.82 (d, 1H, J=6 Hz), 5.50 (dd, 1H, J=5 Hz, J=8 Hz), 5.28 (brs, 2H), 4.07 (q, 2H, J=5 Hz), 3.86 (s, 3H), 3.77 (dd, 1H, J=8 Hz, J=12 Hz), 3.22 (dd, 1H, J=5 Hz, J=12 Hz), 1.44 (t, 3H, J=5 Hz).

Example 39

3-(3,4-dimethoxy-phenyl)-3-(1-amino-4,6-dioxo-4H-thiophene[3,4-c]pyrrole-5(6H)-yl)propionitrile The title compound was prepared following the method of Example 38 except that Intermediate 28 was substituted with Intermediate 29. $^1H$ NMR ($CDCl_3$): δ 7.02 (s, 2H), 6.90 (s, 1H), 6.80 (d, 1H, J=6 Hz), 5.49 (dd, 1H, J=5 Hz, J=8 Hz), 5.31 (brs, 2H), 3.85 (s, 3H), 3.84 (s, 3H), 3.75 (dd, 1H, J=8 Hz, J=12 Hz), 3.22 (dd, 1H, J=5 Hz, J=12 Hz).

Example 40

3-(3-Methoxy-4-benzyloxy phenyl)-3-(1-amino-4,6-dioxo-4H-thiophene[3,4-c]pyrrole-5(6H)-yl)propionitrile The title compound was prepared following the method of Example 38 except that Intermediate 28 was substituted with Intermediate 30. $^1H$ NMR ($CDCl_3$): δ 7.28-7.41 (m, 5H), 7.04 (s, 1H), 6.96 (d, 1H, J=6 Hz), 6.90 (s, 1H), 6.82 (d, 1H, J=6 Hz), 5.47 (dd, 1H, J=5 Hz, J=8 Hz), 5.26 (brs, 2H), 5.12 (s, 2H), 3.88 (s, 3H), 3.75 (dd, 1H, J=8 Hz, J=12 Hz), 3.20 (dd, 1H, J=5 Hz, J=12 Hz).

Example 41

3-(3-Ethoxy-4-methoxy-phenyl)-3-(1-amino-4,6-dioxo-4H-thiophene[3,4-c]pyrrole-5(6H)-yl)propionitrile The title compound was prepared following the method of Example 38 except that Intermediate 28 was substituted with Intermediate 31. $^1H$ NMR ($CDCl_3$—$CD_3OD$): δ 7.05 (s, 1H), 6.91 (s, 1H), 6.85 (d, 1H, J=6 Hz), 5.49 (dd, 1H, J=5 Hz, J=8 Hz), 4.09 (q, 2H, J=5 Hz), 3.85 (s, 3H), 3.80 (dd, 1H, J=8 Hz, J=12 Hz), 3.26 (dd, 1H, J=5 Hz, J=12 Hz), 1.46 (t, 3H, J=5 Hz).

Example 42

3-(3-Cyclopentyloxy-4-methoxy-phenyl)-3-(1-amino-4,6-dioxo-4H-thiophene[3,4-c]pyrrole-5(6H)-yl)propionitrile The title compound was prepared following the method of Example 38 except that Intermediate 28 was substituted with Intermediate 32. $^1H$ NMR ($CDCl_3$): δ 7.05 (s, 1H), 7.01 (d, 1H, J=6 Hz), 6.91 (s, 1H), 6.81 (t, 1H, J=6 Hz), 5.49 (dd, 1H, J=5 Hz, J=8 Hz), 5.29 (brs, 2H), 4.74-4.77 (m, 1H), 3.82 (s, 3H), 3.77 (dd, 1H, J=8 Hz, J=12 Hz), 3.22 (dd, 1H, J=5 Hz, J=12 Hz), 1.60-1.96 (m, 8H).

Example 43

3-(3-Methoxy-4-benzyloxy phenyl)-3-(4,6-dioxo-4H-thiophene[3,4-c]pyrrole-5(6H)-yl)propionamide To a 50 mL round bottom flask equipped with an electromagnetic stirrer and a drying tube, 0.12 g of Intermediate 33, 0.062 g of Intermediate 3, and 10 mL of dry DMF were added. The solution was stirred overnight at room temperature. 0.07 g of CDI were added, and the reaction mixture was allowed to react at 70° C. for 6 hours. Then, 100 mL of water was added to the solution, and the solution was extracted with 50 mL of $CHCl_3$. The resultant organic layer was washed successively with saturated $NaHCO_3$, water, 1N hydrochloric acid, water, and saturated brine, dried over anhydrous $MgSO_4$, filtered, evaporated, and purified by column chromatography to give 0.122 g of white solid. $^1H$ NMR ($CDCl_3$): δ 7.77 (s, 2H), 7.26-7.41 (m, 5H), 7.10 (s, 1H), 7.00 (d, 1H, J=6 Hz), 6.79 (d, 1H, J=6 Hz), 5.72 (dd, 1H, J=5 Hz, J=8 Hz), 5.65 (s, 1H), 5.58 (s, 1H), 5.12 (s, 2H), 3.88 (s, 3H), 3.67 (dd, 1H, J=8 Hz, J=12 Hz), 3.02 (dd, 1H, J=5 Hz, J=12 Hz).

Example 44

N-methyl 3-(3-Methoxy-4-benzyloxy phenyl)-3-(4,6-dioxo-4H-thiophene[3,4-c]pyrrole-5(6H)-yl)propionamide The title compound was prepared following the method of Example 43 except that Intermediate 33 was substituted with Intermediate 34. $^1H$ NMR ($CDCl_3$): δ 7.80 (s, 2H), 7.29-7.42 (m, 5H), 7.10 (s, 1H), 7.00 (d, 1H, J=6 Hz), 6.81 (d, 1H, J=6 Hz), 5.73 (dd, 1H, J=5 Hz, J=8 Hz), 5.12 (s, 2H), 3.88 (s, 3H), 3.55 (dd, 1H, J=8 Hz, J=12 Hz), 3.00 (dd, 1H, J=5 Hz, J=12 Hz), 2.70 (s, 3H).

Example 45

N-ethyl 3-(3-Methoxy-4-benzyloxy phenyl)-3-(4,6-dioxo-4H-thiophene[3,4-c]pyrrole-5(6H)-yl)propionamide The title compound was prepared following the method of Example 43 except that Intermediate 33 was substituted with Intermediate 35. $^1H$ NMR ($CDCl_3$): δ 7.76 (s, 2H), 7.26-7.41 (m, 5H), 7.10 (s, 1H), 7.00 (d, 1H, J=6 Hz), 6.79 (d, 1H, J=6 Hz), 5.73 (dd, 1H, J=5 Hz, J=8 Hz), 5.12 (s, 2H), 3.87 (s, 3H), 3.56 (dd, 1H, J=8 Hz, J=12 Hz), 3.15-3.23 (m, 2H), 2.94 (dd, 1H, J=5 Hz, J=12 Hz), 0.97 (t, 3H, J=6 Hz).

Example 46

N-phenyl 3-(3-Methoxy-4-benzyloxy phenyl)-3-(4,6-dioxo-4H-thiophene[3,4-c]pyrrole-5(6H)-yl)propionamide The title compound was prepared following the method of Example 43 except that Intermediate 33 was substituted with Intermediate 36. MS (m/z): 511 [M−1]$^+$.

Example 47

N-benzyl 3-(3-Ethoxy-4-methoxy-phenyl)-3-(4,6-dioxo-4H-thiophene[3,4-c]pyrrole-5(6H)-yl)propionamide The title compound was prepared following the method of Example 43 except that Intermediate 33 was substituted with Intermediate 37. $^1$H NMR (CDCl$_3$): δ 7.72 (s, 2H), 7.06-7.16 (m, 7H), 6.79 (d, 1H, J=6 Hz), 5.91 (s, 1H), 5.77 (dd, 1H, J=3 Hz, J=5 Hz), 4.45 (dd, 1H, J=3 Hz, J=7 Hz), 4.28 (dd, 1H, J=3 Hz, J=7 Hz), 4.08 (q, 2H, J=3 Hz), 3.83 (s, 3H), 3.62 (dd, 1H, J=5 Hz, J=7 Hz), 3.04 (dd, 1H, J=3 Hz, J=7 Hz), 1.43 (t, 3H, J=3 Hz).

Example 48

5-(1-(3-Methoxy-4-ethoxy-phenyl)-3-hydroxypropyl)-5H-thiophene[3,4-c]pyrrole-4,6-dione To a 50 mL round bottom flask equipped with an electromagnetic stirrer and a drying tube, 0.045 g of Intermediate 38, 0.031 g of Intermediate 3, and 10 mL of dry THF were added. The solution was stirred overnight at room temperature, and 0.04 g of CDI was added. The reaction mixture was refluxed for 6 hours. The solution was evaporated to remove solvent, and extracted with 40 mL of CHCl$_3$. The resultant organic layer was washed successively with saturated NaHCO$_3$, water, 1N hydrochloric acid, water, and saturated brine, dried over anhydrous MgSO$_4$, filtered, evaporated, and purified by column chromatography to give 0.042 g of white solid. $^1$H NMR (CDCl$_3$): δ 7.78 (s, 2H), 7.12 (s, 1H), 7.08 (d, 1H, J=6 Hz), 6.81 (d, 1H, J=6 Hz), 5.47 (dd, 1H, J=5 Hz, J=8 Hz), 4.07 (q, 2H, J=5 Hz), 3.87 (s, 3H), 3.65-3.73 (m, 2H), 2.70-2.79 (m, 1H), 2.47-2.55 (m, 1H), 1.44 (t, 3H, J=5 Hz).

Example 49

5-(1-(3-Ethoxy-4-methoxy-phenyl)-3-hydroxypropyl)-5H-thiophene[3,4-c]pyrrole-4,6-dione The title compound was prepared following the method of Example 48 except that Intermediate 38 was substituted with Intermediate 39. MS (m/z): 362 [M+1]$^+$.

Example 50

5-(1-(3-Methoxy-4-benzyloxy phenyl)-3-oxo-3-(piperidine-1-yl)propyl)-5H-thiophene[3,4-c]pyrrole-4,6-dione To a 50 mL round bottom flask equipped with an electromagnetic stirrer and a drying tube, 0.21 g of Intermediate 41, 0.088 g of Intermediate 3, and 10 mL of dry THF were added. The solution was stirred overnight at room temperature, and 0.148 g of CDI were added. The reaction mixture was refluxed for 6 hours. The solution was evaporated to remove the solvent, and extracted with 70 mL of CHCl$_3$. The resultant organic layer was washed successively with saturated NaHCO$_3$, water, 1N hydrochloric acid, water and saturated brine, dried over anhydrous MgSO$_4$, filtered, evaporated, and purified by column chromatography to give 0.27 g of a solid.
$^1$H NMR (CDCl$_3$): δ 7.74 (s, 2H), 7.26-7.41 (m, 5H), 7.13 (s, 1H), 7.03 (d, 1H, J=6 Hz), 6.80 (d, 1H, J=6 Hz), 5.76 (dd, 1H, J=4 Hz, J=8 Hz), 5.12 (s, 2H), 3.88 (s, 3H), 3.85 (dd, 1H, J=8 Hz, J=12 Hz), 3.41-3.51 (m, 4H), 3.03 (dd, 1H, J=4 Hz, J=12 Hz), 1.47-1.60 (m, 6H).

Example 51

N,N-dimethyl 3-(3-Methoxy-4-benzyloxy phenyl)-3-(4,6-dioxo-4H-thiophene[3,4-c]pyrrole-5(6H)-yl) propionamide The title compound was prepared following the method of Example 50 except that Intermediate 41 was substituted with Intermediate 42. $^1$H NMR (CDCl$_3$): δ 7.75 (s, 2H), 7.27-7.42 (m, 5H), 7.14 (s, 1H), 7.04 (d, 1H, J=6 Hz), 6.81 (d, 1H, J=6 Hz), 5.77 (dd, 1H, J=4 Hz, J=8 Hz), 5.13 (s, 2H), 3.89 (s, 3H), 3.86 (dd, 1H, J=8 Hz, J=12 Hz), 3.03 (s, 3H), 3.00 (dd, 1H, J=4 Hz, J=12 Hz), 2.90 (s, 3H).

Example 52

N,N-diethyl 3-(3-Methoxy-4-benzyloxy phenyl)-3-(4,6-dioxo-4H-thiophene[3,4-c]pyrrole-5(6H)-yl) propionamide The title compound was prepared following the method of Example 50 except that Intermediate 41 was substituted with Intermediate 43. $^1$H NMR (CDCl$_3$): δ 7.75 (s, 2H), 7.27-7.42 (m, 5H), 7.14 (s, 1H), 7.04 (d, 1H, J=6 Hz), 6.81 (d, 1H, J=6 Hz), 5.80 (dd, 1H, J=5 Hz, J=8 Hz), 5.13 (s, 2H), 3.89 (s, 3H), 3.87 (dd, 1H, J=8 Hz, J=12 Hz), 3.26-3.37 (m, 4H), 3.01 (dd, 1H, J=5 Hz, J=12 Hz), 1.17 (t, 3H, J=6 Hz), 1.02 (t, 3H, J=6 Hz).

Example 53

N-methyl-N-phenyl 3-(3-Methoxy-4-benzyloxy phenyl)-3-(4,6-dioxo-4H-thiophene[3,4-c]pyrrole-5(6H)-yl)propionamide The title compound was prepared following the method of Example 50 except that Intermediate 41 was substituted with Intermediate 44. $^1$H NMR (CDCl$_3$): δ 7.74 (s, 2H), 7.15-7.44 (m, 10H), 6.93 (s, 1H), 6.83 (d, 1H, J=6 Hz), 6.72 (d, 1H, J=6 Hz), 5.70 (dd, 1H, J=4 Hz, J=8 Hz), 5.08 (s, 2H), 3.80 (s, 3H), 3.51 (dd, 1H, J=8 Hz, J=12 Hz), 3.19 (s, 3H), 2.84 (dd, 1H, J=4 Hz, J=12 Hz).

Example 54

5-(1-(3-Methoxy-4-benzyloxy phenyl)-3-dimethylamino-propyl)-5H-thiophene[3,4-c]pyrrole-4,6-dione To a 50 mL round bottom flask equipped with an electromagnetic stirrer and a drying tube, 0.076 g of Intermediate 47, 0.038 g of Intermediate 3, and 10 mL of dry THF were added. The solution was stirred overnight at room temperature. 0.095 g of CDI was added, and the resultant mixture was refluxed for 6 hours. Solvent was evaporated in vacuo and the residue was extracted with 50 mL of ethyl acetate. The organic layer was washed successively with saturated NaHCO$_3$, water, and saturated brine, dried over anhydrous MgSO$_4$, filtered, evaporated, and purified by column chromatography to give 0.047 g of a solid. $^1$H NMR (CDCl$_3$): δ 7.76 (s, 2H), 7.26-7.43 (m, 5H), 7.15 (s, 1H), 7.02 (d, 1H, J=3 Hz), 6.81 (d, 1H, J=4 Hz), 5.28 (dd, 1H, J=3 Hz, J=4 Hz), 5.12 (s, 2H), 3.89 (s, 3H), 2.63-2.74 (m, 1H), 2.35-2.41 (m, 1H), 2.20-2.31 (m, 8H); MS (m/z): 451 [M+1]$^+$.

Example 55

5-(1-(3-Methoxy-4-benzyloxy phenyl)-3-diethylamino-propyl)-5H-thiophene[3,4-c]pyrrole-4,6-dione The title compound was prepared following the method of Example 54 except that Intermediate 47 was substituted with Intermediate 48. MS (m/z): 479 [M+1]$^+$.

Example 56

5-(1-(3-Methoxy-4-benzyloxy phenyl)-3-(piperidine-1-yl)propyl)-5H-thiophene[3,4-c]pyrrole-4,6-dione The title compound was prepared following the method of Example 54 except that Intermediate 47 was substituted with Intermediate 49. MS (m/z): 491 [M+1]$^+$.

Example 57

3-(3-Ethoxy-4-methoxy-phenyl)-3-(4,6-dioxo-4H-thiophene[3,4-c]pyrrole-5(6H)-yl)propionic acid 0.78 g of 3-(3-ethoxy-4-methoxy-phenyl)-3-(4,6-dioxo-4H-thiophene[3,4-c]pyrrole-5(6H)-yl)methyl propionate (prepared following the method of Example 2) was dissolved in 10 mL of THF, and 10 mL of 1N LiOH solution was added. The solution was stirred at room temperature for 2 hours, and 1N hydrochloric acid was added to adjust the pH value to 1. The resultant solution was extracted with 70 mL of ethyl acetate, and the obtained organic layer was washed successively with 30 mL of water and saturated brine, dried over anhydrous MgSO$_4$, filtered, and evaporated to give 0.71 g of 4-((2-carboxyl-1-(3-ethoxy-4-methoxyphenyl)ethyl)amino formyl)thiophene-3-carboxylic acid. $^1$H NMR (CDCl$_3$): δ 8.23 (d, 1H, J=2 Hz), 8.11 (d, 1H, J=2 Hz), 6.86 (s, 1H), 6.83 (d, 1H, J=6 Hz), 6.72 (t, 1H, J=6 Hz), 5.38 (dd, 1H, J=5 Hz, J=6 Hz), 3.97 (q, 2H, J=5 Hz), 3.72 (s, 3H), 2.84 (dd, 1H, J=6 Hz, J=12 Hz), 2.73 (dd, 1H, J=5 Hz, J=12 Hz), 1.31 (t, 3H, J=5 Hz); MS (m/z): 392 [M−1]$^+$.

0.296 g of 4-((2-carboxyl-1-(3-ethoxy-4-methoxyphenyl)ethyl)amino formyl)thiophene-3-carboxylic acid was dissolved in 10 mL of dry THF, and 0.243 g of CDI was added. The reaction mixture was refluxed for 6 hours. The solvent was evaporated, and 70 mL of ethyl acetate and 20 mL of 1N hydrochloric acid were added. The resultant organic layer was washed successively with 1N hydrochloric acid, water and saturated brine, dried over anhydrous MgSO$_4$, filtered, evaporated, and purified by column chromatography to give 0.147 g of a solid. $^1$H NMR (CDCl$_3$): δ 7.67 (s, 2H), 7.37 (d, 1H, J=3 Hz), 7.07 (s, 1H), 7.02 (d, 1H, J=6 Hz), 6.77 (d, 1H, J=6 Hz), 5.65 (s, 1H), 4.08 (q, 2H, J=5 Hz), 3.82 (s, 3H), 3.70-3.72 (m, 1H), 3.07-3.10 (m, 1H), 1.44 (t, 3H, J=5 Hz); MS (m/z): 374 [M−1]$^+$.

Example 58

3-(3-Methoxy-4-ethoxy-phenyl)-3-(4,6-dioxo-4H-thiophene[3,4-c]pyrrole-5(6H)-yl)propionic acid The title compound was prepared following the method of Example 57 except that 3-(3-ethoxy-4-methoxy-phenyl)-3-(4,6-dioxo-4H-thiophene[3,4-c]pyrrole-5(6H)-yl)methyl propionate (prepared following the method of Example 2) was substituted with 3-(3-methoxy-4-ethoxy-phenyl)-3-(4,6-dioxo-4H-thiophene[3,4-c]pyrrole-5(6H)-yl)methyl propionate (prepared following the method of Example 7). MS (m/z): 374 [M−1]$^+$.

Example 59

3-(3-Methoxy-4-ethoxy-phenyl)-3-(4,6-dioxo-4H-thiophene[3,4-c]pyrrole-5(6H)-yl)-N-hydroxy propionamide To a 100 mL round bottom flask equipped with an electromagnetic stirrer and a drying tube, 0.375 g of 3-(3-methoxy-4-ethoxy-phenyl)-3-(4,6-dioxo-4H-thiophene[3,4-c]pyrrole-5(6H)-yl)propionic acid, 0.149 g of BTOH, and 10 mL of dry THF were added. The solution was cooled on an ice bath and 0.227 g of DCC were added. The solution was stirred overnight at room temperature, and cyclohexyl urea was removed by filtration to obtain a filtrate. 0.139 g of hydroxylamine hydrochloride and 0.252 g of NaHCO$_3$ were dissolved in 5 mL of water, and the resultant solution was added to the above-mentioned filtrate. The mixture was stirred for 5 minutes, and THF was evaporated. 1N hydrochloric acid added to adjust the pH value to 4. Then, the solution was extracted with 70 mL of CHCl$_3$ and the organic layer was washed successively with water and saturated brine, dried over anhydrous MgSO$_4$, filtered, evaporated, and purified by column chromatography to give 0.09 g of white solid. MS (m/z): 389 [M−1]$^+$.

Example 60

3-(3-Methoxy-4-ethoxy-phenyl)-3-(4,6-dioxo-4H-thiophene[3,4-c]pyrrole-5(6H)-yl)propionamide The title compound was prepared following the method of Example 59 except that hydroxylamine hydrochloride was substituted with hydrazine hydrate. MS (m/z): 779 [2M+1]$^+$.

Example 61

5-(1-(3-Ethoxy-4-methoxy-phenyl)-3-methoxy-propyl)-5H-thiophene[3,4-c]pyrrole-4,6-dione To a 50 mL round bottom flask equipped with an electromagnetic stirrer and a drying tube, 0.085 g of Intermediate 52, 0.055 g of Intermediate 3, and 10 mL of dry THF were added. The solution was stirred overnight at room temperature, and 0.1 g of CDI was added. The reaction mixture was refluxed for 6 hours. The solvent was removed in vacuo, and the residue was extracted with 40 mL of ethyl acetate. The resultant organic layer was washed successively with saturated NaHCO$_3$, water, 1N hydrochloric acid, water, and saturated brine, dried over anhydrous MgSO$_4$, filtered, evaporated, and purified by column chromatography to give a solid. $^1$H NMR (CDCl$_3$): δ 7.77 (s, 2H), 7.14 (s, 1H), 7.08 (d, 1H, J=6 Hz), 6.81 (d, 1H, J=6 Hz), 5.40 (dd, 1H, J=5 Hz, J=11 Hz), 4.11 (q, 2H, J=5 Hz), 3.84 (s, 3H), 3.91 (t, 2H, J=5 Hz), 3.27 (s, 3H), 2.76 (dd, 1H, J=5 Hz, J=11 Hz), 2.52 (dd, 1H, J=5 Hz, J=11 Hz), 1.45 (t, 3H, J=5 Hz).

Example 62 methyl 3-(3-Ethoxy-4-methoxy-phenyl)-3-(4-oxo-4H-thiophene[3,4-c]pyrrole-5(6H)-yl)propionate To a 50 mL round bottom flask equipped with an electromagnetic stirrer and a drying tube, 0.506 g of Intermediate 7, 0.324 g of Intermediate 55, 0.414 g of $K_2CO_3$, and 10 mL of dry DMF were added. The solution was stirred overnight at room temperature, and then 50 mL of ethyl acetate and 100 mL of water added. The organic layer was washed successively with water and saturated brine, dried over anhydrous $MgSO_4$, filtered, evaporated, and purified by column chromatography to give 0.335 g of oil-like product.

The product was dissolved in 6 mL of DCM and 2 mL of TFA, and the resultant solution was stirred overnight at room temperature. The solvent was evaporated, and the residue was dissolved in 8 mL of dry DCM. The pH value was adjusted to 9 with dried TEA. To the solution 0.338 g of DCC was added. The resultant reaction mixture was stirred overnight at room temperature. Cyclohexyl urea was removed by filtration, and the solvent evaporated. Then 50 mL of ethyl acetate was added to dissolve the residue, and the organic layer was washed successively with saturated $NaHCO_3$ solution, water, 1N hydrochloric acid, water and saturated brine, dried over anhydrous $MgSO_4$, filtered, evaporated, and purified by column chromatography to give 0.203 g of a white solid. $^1$H NMR (CDCl$_3$): δ 7.70 (d, 1H, J=1 Hz), 7.02 (s, 1H), 6.92 (s, 1H), 6.89 (d, 1H, J=6 Hz), 6.83 (d, 1H, J=6 Hz), 5.85 (t, 1H, J=6 Hz), 4.26 (d, 1H, J=12 Hz), 4.03-4.09 (m, 2H), 3.95 (d, 1H, J=12 Hz), 3.85 (s, 3H), 3.64 (s, 3H), 3.17 (dd, 1H, J=7 Hz, J=12 Hz), 3.08 (dd, 1H, J=5 Hz, J=12 Hz), 1.44 (t, 3H, J=5 Hz); MS (m/z): 376 [M+1]$^+$.

Example 63 methyl 3-(3-Methoxy-4-ethoxy-phenyl)-3-(4-oxo-4H-thiophene[3,4-c]pyrrole-5(6H)-yl)propionate The title compound was prepared following the method of Example 62 except that Intermediate 7 was substituted with Intermediate 12. $^1$H NMR (CDCl$_3$): δ 7.72 (d, 1H, J=2 Hz), 7.02 (t, 1H, J=1 Hz), 6.81-6.91 (m, 3H), 5.85 (dd, 1H, J=6 Hz, J=7 Hz), 4.26 (d, 1H, J=12 Hz), 4.08 (q, 2H, J=5 Hz), 3.95 (d, 1H, J=12 Hz), 3.84 (s, 3H), 3.65 (s, 3H), 3.17 (dd, 1H, J=7 Hz, J=12 Hz), 3.07 (dd, 1H, J=5 Hz, J=12 Hz), 1.45 (t, 3H, J=5 Hz); MS (m/z): 376 [M+1]$^+$.

Example 64

3-(3-Ethoxy-4-methoxy-phenyl)-3-(4-oxo-4H-thiophene[3,4-c]pyrrole-5(6H)-yl)propionitrile The title compound was prepared following the method of Example 62 except that Intermediate 7 was substituted with Intermediate 31. $^1$H NMR (CDCl$_3$): δ 7.78 (d, 1H, J=2 Hz), 7.04 (d, 1H, J=1 Hz), 6.83-6.96 (m, 3H), 5.64 (t, 1H, J=5 Hz), 4.32 (d, 1H, J=12 Hz), 4.07 (q, 2H, J=5 Hz), 3.95 (d, 1H, J=12 Hz), 3.88 (s, 3H), 3.20 (dd, 1H, J=5 Hz, J=12 Hz), 3.14 (dd, 1H, J=3 Hz, J=10 Hz), 1.45 (t, 3H, J=5 Hz); MS (m/z): 365 [M+Na]$^+$.

Example 65

3-(3-Cyclopentyloxy-4-methoxy-phenyl)-3-(4-oxo-4H-thiophene[3,4-c]pyrrole-5(6H)-yl)propionitrile The title compound was prepared following the method of Example 62 except that Intermediate 7 was substituted with Intermediate 32. $^1$H NMR (CDCl$_3$): δ 7.78 (d, 1H, J=2 Hz), 7.05 (d, 1H, J=1 Hz), 6.94 (s, 1H), 6.92 (s, 1H), 6.86 (d, 1H, J=5 Hz), 5.64 (t, 1H, J=5 Hz), 4.73-4.77 (m, 2H), 4.33 (d, 1H, J=12 Hz), 3.96 (d, 1H, J=12 Hz), 3.85 (s, 3H), 3.20 (dd, 1H, J=8 Hz, J=12 Hz), 3.16 (dd, 1H, J=5 Hz, J=12 Hz), 1.58-1.89 (m, 8H); MS (m/z): 381 [M−1]$^+$.

Example 66

3-(3-Methoxy-4-ethoxy-phenyl)-3-(4-oxo-4H-thiophene[3,4-c]pyrrole-5(6H)-yl)propionitrile The title compound was prepared following the method of Example 62 except that Intermediate 7 was substituted with Intermediate 28. $^1$H NMR (CDCl$_3$): δ 7.77 (d, 1H, J=2 Hz), 7.04 (dt, 1H, J=1 Hz), 6.84-6.96 (m, 3H), 5.64 (t, 1H, J=5 Hz), 4.32 (d, 1H, J=12 Hz), 4.09 (q, 2H, J=5 Hz), 3.95 (d, 1H, J=12 Hz), 3.84 (s, 3H), 3.13-3.21 (m, 2H), 1.46 (t, 3H, J=5 Hz); MS (m/z): 343 [M+1]$^+$.

Example 67

3-(3-Ethoxy-4-methoxy-phenyl)-3-(4,6-dioxo-4H-thiophene[3,4-c]pyrrole-5(6H)-yl)propyl-methyl sulfoxide The title compound was prepared following the method of Example 23 except that Intermediate 6 was substituted with Intermediate 57. MS (m/z): 408 [M+1]$^+$.

Example 68

3-(3-Ethoxy-4-methoxy-phenyl)-3-(4,6-dioxo-4H-thiophene[3,4-c]pyrrole-5(6H)-yl)propionaldehyde oxime methyl ether The title compound was prepared following the method of Example 23 except that Intermediate 6 was substituted with Intermediate 61. MS (m/z): 389 [M+1]$^+$.

Example 69

3-(3-Ethoxy-4-methoxy-phenyl)-3-(4,6-dioxo-4H-thiophene[3,4-c]pyrrole-5(6H)-yl)butan-2-ol The title compound was prepared following the method of Example 23 except that Intermediate 6 was substituted with Intermediate 64. MS (m/z): 376 [M+1]$^+$.

Example 70

3-(3-Ethoxy-4-methoxy-phenyl)-3-(4,6-dioxo-4H-thiophene[3,4-c]pyrrole-5(6H)-yl)butan-2-one The title compound was prepared following the method of Example 23 except that Intermediate 6 was substituted with Intermediate 65. MS (m/z): 374 [M+1]$^+$.

Example 71 methyl 3-(4-Pyridyl)-3-(4,6-dioxo-4H-thiophene[3,4-c]pyrrole-5(6H)-yl)propionate The title compound was prepared following the method of Example 23 except that Intermediate 6 was substituted with Intermediate 66. MS (m/z): 317 [M+1]$^+$.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A compound of Formula (I) or Formula (II), a pharmaceutically acceptable salt, or hydrate thereof,

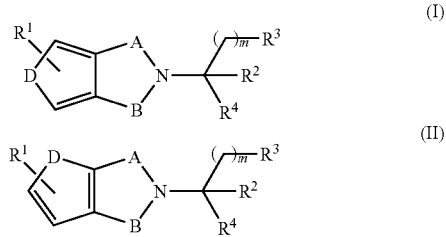

wherein
A and B independently represent $CH_2$, CO, SO, or $SO_2$;
D represents S, NH, or $NC_{1-6}$alkyl;
$R^1$ represents H, or one or two same or different occurrences of F, Cl, Br, $C_{1-4}$alkyl, OH, $OC_{1-4}$alkyl, $NO_2$, $NHC(O)C_{1-4}$alkyl, $NH_2$, $NH(C_{1-4}$alkyl), or $N(C_{1-4}$alkyl$)_2$;
$R^2$ at each occurrence represents F, $CF_3$, H, or $C_{1-4}$alkyl;
$R^3$ at each occurrence represents OH, $CH(OH)C_{1-4}$alkyl, $OC_{1-4}$alkyl, $NHC(O)C_{1-4}$alkyl, $NH_2$, $NH(C_{1-4}$alkyl), $N(C_{1-4}$alkyl$)_2$, $C(O)OC_{1-4}$alkyl, $C(O)NH_2$, $C(O)NH(C_{1-4}$alkyl), $C(O)N(C_{1-4}$alkyl$)_2$, C(O)NHOH, $C(O)NH(OC_{1-4}$alkyl), $C(O)C_{1-4}$alkyl, $S(O)C_{1-4}$alkyl, $SO_2C_{1-4}$alkyl, $SO_2NHC_{1-4}$alkyl, $NHSO_2C_{1-4}$alkyl, $NHC(O)C_{1-4}$alkyl, CN, CH=NOH, CH=N($OC_{1-4}$alkyl), $C(C_{1-4}$alkyl)=NOH, $C(C_{1-4}$alkyl)=N($OC_{1-4}$alkyl), CH=NCN, CH=NC(O)$C_{1-4}$alkyl, CH=C(CN)$_2$, CH=CHNO$_2$, C(=NH)NH($C_{1-4}$alkyl), $C(C_{1-4}$alkyl)=NCN, $C(C_{1-4}$alkyl)=NC(O)$C_{1-4}$alkyl, $C(C_{1-4}$alkyl)=C(CN)$_2$, or $C(C_{1-4}$alkyl)=CHNO$_2$;
$R^4$ represents $C_{1-8}$alkylhydrocarbyl, or $(CH_2)_n$Ar—$R^5$;
Ar represents a 4- to 8-membered hydrocarbon ring or an aromatic ring containing from 0 to 4 heteroatoms;
$R^5$ represents H, 1 to 4 same or different F, $CF_3$, CN, Cl, $C_{1-4}$alkyl, OH, $OC_{1-4}$alkyl, $NHC(O)C_{1-4}$alkyl, $NH_2$, $NH(C_{1-4}$alkyl), $N(C_{1-4}$alkyl$)_2$, $C(O)OC_{1-4}$alkyl, $OOCC_{1-4}$alkyl, $C(O)NH_2$, $C(O)NH(C_{1-4}$alkyl), $C(O)N(C_{1-4}$alkyl$)_2$, $C(O)C_{1-4}$alkyl, $S(O)C_{1-4}$alkyl, $SO_2C_{1-4}$alkyl, $O_2CC_{1-4}$alkyl, E, or W—$(CH_2)_l$E;
E represents a 4- to 8-membered hydrocarbon ring or an aromatic ring containing 0 to 4 heteroatoms;
W represents O, S, NH, or $CH_2$;
l represents 0, 1, 2, 3, or 4;
m represents 0, 1, 2, 3, 4, 5, or 6; and
n represents 0, 1, 2, 3 or 4.

2. The compound of claim 1, wherein A and B independently represent $CH_2$, or CO.

3. The compound of claim 1, wherein D represents S.

4. The compound of claim 1, wherein W represents 0.

5. The compound of claim 1, wherein 1 and n independently represent 0, 1, or 2.

6. The compound of claim 1, wherein m represents 1, 2, or 3.

7. The compound of claim 1, wherein $R^1$ represents H, F, $NO_2$, $NH_2$, $NHCH_3$, $N(CH_3)_2$, $NHCOCH_3$, OH, or $OCH_3$.

8. The compound of claim 1, wherein $R^2$ represents H, F, or $CH_3$.

9. The compound of claim 1, wherein $R^3$ represents OH, $CH(OH)CH_3$, $CH(OH)CH_2CH_3$, $OCH_3$, $OCH_2CH_3$, $OCH(CH_3)_2$, $OCH_2CH_2CH_3$, $C(O)CH_3$, $C(O)CH_2CH_3$, $C(O)CH_2CH_2CH_3$, $C(O)CH(CH_3)_2$, $COOCH_3$, $COOCH_2CH_3$, $COOCH_2CH_2CH_3$, $COOCH(CH_3)_2$, $S(O)CH_3$, $S(O)CH_2CH_3$, $SO_2CH_3$, $SO_2CH_2CH_3$, $C(O)NH_2$, $C(O)NHCH_3$, $C(O)NHCH_2CH_3$, $C(O)NHCH_2CH_2CH_3$, $C(O)N(CH_3)_2$, $C(O)NEt_2$, C(O)-1-piperidine, C(O)NHOH, C(O)NH(OMe), C(O)NH(OEt), CN, CH=NOH, CH=NOMe, CH=NOEt, or CH=NCN.

10. The compound of claim 1, wherein Ar and E independently represent phenyl, naphthalyl, pyridyl, pyrimidinyl, thiophene, furyl, indolyl, isoindolyl, benzo-thiophene, or benzofuryl.

11. The compound of claim 1, wherein $R^5$ represents H, or from 1 to 4 same or different at each occurrences of F, Cl, methyl, ethyl, trifluoromethyl, OH, $OCH_3$, ethoxy, isopropoxy, propoxy, butoxy, cyclopentyloxy, benzyloxy, NHC(O)Me, $NH_2$, methylamino, ethylamino, dimethylamino, CN, $COOCH_3$, $COOCH_2CH_3$, $COOCH_2CH_2CH_3$, $COOCH(CH_3)_2$, $OOCCH_3$, $OOCCH_2CH_3$, $C(O)NH_2$, $C(O)NHCH_3$, $C(O)NHCH_2CH_3$, $C(O)NHCH_2CH_2CH_3$, or $C(O)N(CH_3)_2$.

12. A pharmaceutical composition at least comprising a compound of Formula (I) or (II),

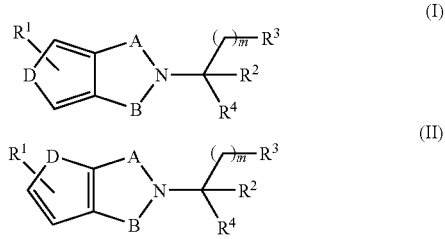

wherein
A and B independently represent $CH_2$, CO, SO, or $SO_2$;
D represents S, NH, or $NC_{1-6}$ alkyl;
$R^1$ represents H, or one or two same or different occurrences of F, Cl, Br, $C_{1-4}$alkyl, OH, $OC_{1-4}$alkyl, $NO_2$, $NHC(O)C_{1-4}$alkyl, $NH_2$, $NH(C_{1-4}$alkyl), or $N(C_{1-4}$alkyl$)_2$;
$R^2$ at each occurrence represents F, $CF_3$, H, or $C_{1-4}$alkyl;
$R^3$ at each occurrence represents OH, $CH(OH)C_{1-4}$alkyl, $OC_{1-4}$alkyl, $NHC(O)C_{1-4}$alkyl, $NH_2$, $NH(C_{1-4}$alkyl), $N(C_{1-4}$alkyl$)_2$, $C(O)OC_{1-4}$alkyl, $C(O)NH_2$, $C(O)NH(C_{1-4}$alkyl), $C(O)N(C_{1-4}$alkyl$)_2$, C(O)NHOH, $C(O)NH(OC_{1-4}$alkyl), $C(O)C_{1-4}$alkyl, $S(O)C_{1-4}$alkyl, $SO_2C_{1-4}$alkyl, $SO_2NHC_{1-4}$alkyl, $NHSO_2C_{1-4}$alkyl, $NHC(O)C_{1-4}$alkyl, CN, CH=NOH, CH=N($OC_{1-4}$alkyl), $C(C_{1-4}$alkyl)=NOH, $C(C_{1-4}$alkyl)=N($OC_{1-4}$alkyl), CH=NCN, CH=NC(O)$C_{1-4}$alkyl, CH=C(CN)$_2$, CH=CHNO$_2$, C(=NH)NH($C_{1-4}$alkyl), C($C_{1-4}$alkyl)=NCN, C($C_{1-4}$alkyl)=NC(O)$C_{1-4}$alkyl, C($C_{1-4}$alkyl)=C(CN)$_2$, or C($C_{1-4}$alkyl)=CHNO$_2$;

$R^4$ represents $C_{1-8}$alkyl, or (CH$_2$)$_n$Ar—$R^5$;

Ar represents a 4 to 8-membered hydrocarbon ring or an aromatic ring containing 0 to 4 heteroatoms;

$R^5$ represents H, 1 to 4 same or different F, CF$_3$, CN, Cl, $C_{1-4}$alkyl, OH, NHC(O)$C_{1-4}$alkyl, NH$_2$, NH($C_{1-4}$alkyl), N($C_{1-4}$alkyl)$_2$, C(O)O$C_{1-4}$alkyl, OOC$C_{1-4}$alkyl, C(O)NH$_2$, C(O)NH($C_{1-4}$alkyl), C(O)N($C_{1-4}$alkyl)$_2$, C(O)$C_{1-4}$alkyl, S(O)$C_{1-4}$alkyl, SO$_2$$C_{1-4}$alkyl, O$_2$C$C_{1-4}$alkyl, E, or W—(CH$_2$)$_l$E;

E represents a 4 to 8-membered hydrocarbon ring or an aromatic ring containing 0 to 4 heteroatoms;

W represents O, S, NH, or CH$_2$;

l represents 0, 1, 2, 3, or 4;

m represents 0, 1, 2, 3, 4, 5, or 6; and n represents 0, 1, 2, 3, or 4.

13. A method of alleviating or treating an inflammatory disease or an infectious disease by decreasing the concentration of TNFα in a subject, the method comprising administering to the subject a compound of Formula (I) or Formula (II), a pharmaceutically acceptable salt, or hydrate thereof, wherein A and B independently represent CH$_2$, CO, SO, or SO$_2$;

D represents S, NH, or NC$_{1-6}$ alkyl;

$R^1$ represents H, or one or two same or different occurrences of F, Cl, Br, $C_{1-4}$alkyl, OH, O$C_{1-4}$alkyl, NO$_2$, NHC(O)$C_{1-4}$alkyl, NH$_2$, NH($C_{1-4}$alkyl), or N($C_{1-4}$alkyl)$_2$;

$R^2$ at each occurrence represents F, CF$_3$, H, or $C_{1-4}$alkyl;

$R^3$ at each occurrence represents OH, CH(OH)$C_{1-4}$alkyl, NHC(O)$C_{1-4}$alkyl, NH$_2$, NH($C_{1-4}$alkyl), N($C_{1-4}$alkyl)$_2$, C(O)O$C_{1-4}$alkyl, C(O)NH$_2$, C(O)NH($C_{1-4}$alkyl), C(O)N($C_{1-4}$alkyl)$_2$, C(O)NHOH, C(O)NH(O$C_{1-4}$alkyl), C(O)$C_{1-4}$alkyl, S(O)$C_{1-4}$alkyl, SO$_2$$C_{1-4}$alkyl, SO$_2$NH$C_{1-4}$alkyl, NHSO$_2$$C_{1-4}$alkyl, NHC(O)$C_{1-4}$alkyl, CN, CH=NOH, CH=N(O$C_{1-4}$alkyl), C($C_{1-4}$alkyl)=NOH, C($C_{1-4}$alkyl)=N(O$C_{1-4}$alkyl), CH=NCN, CH=NC(O)$C_{1-4}$alkyl, CH=C(CN)$_2$, CH=CHNO$_2$, C(=NH)NH($C_{1-4}$alkyl), C($C_{1-4}$alkyl)=NCN, C($C_{1-4}$alkyl)=NC(O)$C_{1-4}$alkyl, C($C_{1-4}$alkyl)=C(CN)$_2$, or C($C_{1-4}$alkyl)=CHNO$_2$;

$R^4$ represents $C_{1-8}$alkyl, or (CH$_2$)$_n$Ar—$R^5$,

Ar represents a 4- to 8-membered hydrocarbon ring or an aromatic ring containing 0 to 4 heteroatoms;

$R^5$ represents H, 1 to 4 same or different F, CF$_3$, CN, Cl, $C_{1-4}$alkyl, OH, O$C_{1-4}$alkyl, NHC(O)$C_{1-4}$alkyl, NH$_2$, NH($C_{1-4}$alkyl), N($C_{1-4}$)$_2$, C(O)O$C_{1-4}$alkyl, OOC$C_{1-4}$alkyl, C(O)NH$_2$, C(O)NH($C_{1-4}$alkyl), C(O)N($C_{1-4}$alkyl)$_2$, C(O)$C_{1-4}$alkyl, S(O)$C_{1-4}$alkyl, SO$_2$$C_{1-4}$alkyl, O$_2$C$C_{1-4}$alkyl, E, or W—(CH$_2$)$_l$E;

E represents a 4 to 8-membered hydrocarbon ring or an aromatic ring containing 0 to 4 heteroatoms;

W represents O, S, NH, or CH$_2$;

l represents 0, 1, 2, 3, or 4;

m represents 0, 1, 2, 3, 4, 5, or 6; and n represents 0, 1, 2, 3, or 4.

14. A method of alleviating or treating an immune disease by decreasing the concentration of TNFα in a subject, the method comprising administering to the subject a compound of Formula (I) or Formula (II), a pharmaceutically acceptable salt, or hydrate thereof, wherein A and B independently represent CH$_2$, CO, SO, or SO$_2$;

D represents S, NH, or NC$_{1-6}$ alkyl;

$R^1$ represents H, or one or two same or different occurrences of F, Cl, Br, $C_{1-4}$alkyl, OH, O$C_{1-4}$alkyl, NO$_2$, NHC(O)$C_{1-4}$alkyl, NH$_2$, NH($C_{1-4}$alkyl), or N($C_{1-4}$alkyl)$_2$;

$R^2$ at each occurrence represents F, CF$_3$, H or $C_{1-4}$alkyl;

$R^3$ at each occurrence represents OH, CH(OH)$C_{1-4}$alkyl, O$C_{1-4}$alkyl, NHC(O)$C_{1-4}$alkyl, NH$_2$, NH($C_{1-4}$alkyl), N($C_{1-4}$alkyl)$_2$, C(O)O$C_{1-4}$alkyl, C(O)NH$_2$, C(O)NH($C_{1-4}$alkyl), C(O)N($C_{1-4}$alkyl)$_2$, C(O)NHOH, C(O)NH(O$C_{1-4}$alkyl), C(O)$C_{1-4}$alkyl, S(O)$C_{1-4}$alkyl, SO$_2$$C_{1-4}$alkyl, SO$_2$NH$C_{1-4}$alkyl, NHSO$_2$$C_{1-4}$alkyl, NHC(O)$C_{1-4}$alkyl, CN, CH=NOH, CH=N(O$C_{1-4}$alkyl), C($C_{1-4}$alkyl)=NOH, C($C_{1-4}$alkyl)=N(O$C_{1-4}$alkyl), CH=NCN, CH=NC(O)$C_{1-4}$alkyl, CH=C(CN)$_2$, CH=CHNO$_2$, C(=NH)NH($C_{1-4}$alkyl), C($C_{1-4}$alkyl)=NCN, C($C_{1-4}$alkyl)=NC(O)$C_{1-4}$alkyl, C($C_{1-4}$alkyl)=C(CN)$_2$, or C($C_{1-4}$alkyl)=CHNO$_2$;

$R^4$ represents $C_{1-8}$alkyl, or (CH$_2$)$_n$Ar—$R^5$,

Ar represents a 4- to 8-membered hydrocarbon ring or an aromatic ring containing 0 to 4 heteroatoms;

$R^5$ represents H, 1 to 4 same or different F, CF$_3$, CN, Cl, $C_{1-4}$alkyl, OH, O$C_{1-4}$alkyl, NHC(O)$C_{1-4}$alkyl, NH$_2$, NH($C_{1-4}$alkyl), N($C_{1-}$)$_2$, C(O)O$C_{1-4}$alkyl, OOC$C_{1-4}$alkyl, C(O)NH$_2$, C(O)NH($C_{1-4}$alkyl), C(O)N($C_{1-4}$alkyl)$_2$, C(O)$C_{1-4}$alkyl, S(O)$C_{1-4}$alkyl, SO$_2$$C_{1-4}$alkyl, O$_2$C$C_{1-4}$alkyl, E, or W—(CH$_2$)$_l$E;

E represents a 4 to 8-membered hydrocarbon ring or an aromatic ring containing 0 to 4 heteroatoms;

W represents O, S, NH, or CH$_2$;

l represents 0, 1, 2, 3, or 4;

m represents 0, 1, 2, 3, 4, 5, or 6; and n represents 0, 1, 2, 3 or 4.

15. A method of alleviating or treating a malignant tumor by decreasing the concentration of TNFα in a subject, the method comprising administering to the subject a compound of Formula (I) or Formula (II), a pharmaceutically acceptable salt, or hydrate thereof,

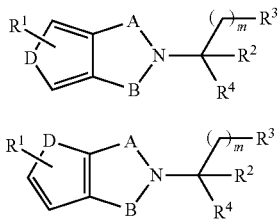

(I)

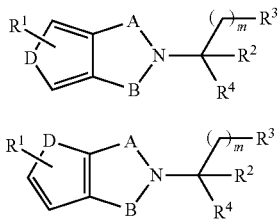

(II)

wherein

A and B independently represent $CH_2$, CO, SO, or $SO_2$;

D represents S, NH, or $NC_{1-6}$ alkyl;

$R^1$ represents H, or one or two same or different occurrences of F, Cl, Br, $C_{1-4}$alkyl, OH, $OC_{1-4}$alkyl, $NO_2$, $NHC(O)C_{1-4}$alkyl, $NH_2$, $NH(C_{1-4}$alkyl$)$, or $N(C_{1-4}$alkyl$)_2$;

$R^2$ at each occurrence represents F, $CF_3$, H, or $C_{1-4}$alkyl;

$R^3$ at each occurrence represents OH, $CH(OH)C_{1-4}$alkyl, $NHC(O)C_{1-4}$alkyl, $NH_2$, $NH(C_{1-4}$alkyl$)$, $N(C_{1-4}$alkyl$)_2$, $C(O)OC_{1-4}$alkyl, $C(O)NH_2$, $C(O)NH(C_{1-4}$alkyl$)$, $C(O)N(C_{1-4}$alkyl$)_2$, $C(O)NHOH$, $C(O)NH(OC_{1-4}$alkyl$)$, $C(O)C_{1-4}$alkyl, $S(O)C_{1-4}$alkyl, $SO_2C_{1-4}$alkyl, $SO_2NHC_{1-4}$alkyl, $NHSO_2C_{1-4}$alkyl, $NHC(O)C_{1-4}$alkyl, CN, CH=NOH, CH=N($OC_{1-4}$alkyl), C($C_{1-4}$alkyl)=NOH, C($C_{1-4}$alkyl)=N($OC_{1-4}$alkyl), CH=NCN, CH=NC(O)$C_{1-4}$alkyl, CH=C(CN)$_2$, CH=CHNO$_2$, C(=NH)NH($C_{1-4}$alkyl), C($C_{1-4}$alkyl)=NCN, C($C_{1-4}$alkyl)=NC(O)$C_{1-4}$alkyl, C($C_{1-4}$alkyl)=C(CN)$_2$, or C($C_{1-4}$alkyl)=CHNO$_2$;

$R^4$ represents $C_{1-8}$alkyl, or $(CH_2)_n Ar-R^5$,

Ar represents a 4- to 8-membered hydrocarbon ring or an aromatic ring containing 0 to 4 heteroatoms;

$R^5$ represents H, 1 to 4 same or different F, $CF_3$, CN, Cl, $C_{1-4}$alkyl, OH, $OC_{1-4}$alkyl, $NHC(O)C_{1-4}$alkyl, $NH_2$, $NH(C_{1-4}$alkyl$)$, $N(C_{1-4})_2$, $C(O)OC_{1-4}$alkyl, $OOCC_{1-4}$alkyl, $C(O)NH_2$, $C(O)NH(C_{1-4}$alkyl$)$, $C(O)N(C_{1-4}$alkyl$)_2$, $C(O)C_{1-4}$alkyl, $S(O)C_{1-4}$alkyl, $SO_2C_{1-4}$alkyl, $O_2CC_{1-4}$alkyl, E, or $W-(CH_2)_l E$;

E represents a 4 to 8-membered hydrocarbon ring or an aromatic ring containing 0 to 4 heteroatoms;

W represents O, S, NH, or $CH_2$;

l represents 0, 1, 2, 3, or 4;

m represents 0, 1, 2, 3, 4, 5, or 6; and n represents 0, 1, 2, 3 or 4.

16. A method of preparing a compound of Formula (I) or Formula (II),

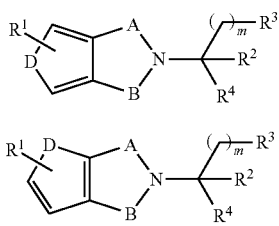

(I)

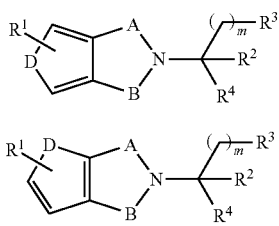

(II)

wherein

A and B independently represent $CH_2$, CO, SO, or $SO_2$;

D represents S, NH, or $NC_{1-6}$ alkyl;

$R^1$ represents H, or one or two same or different occurrences of F, Cl, Br, $C_{1-4}$alkyl, OH, $OC_{1-4}$alkyl, $NO_2$, $NHC(O)C_{1-4}$alkyl, $NH_2$, $NH(C_{1-4}$alkyl$)$, or $N(C_{1-4}$alkyl$)_2$;

$R^2$ at each occurrence represents F, $CF_3$, H, or $C_{1-4}$alkyl;

$R^3$ at each occurrence represents OH, $CH(OH)C_{1-4}$alkyl, $OC_{1-4}$alkyl, $NHC(O)C_{1-4}$alkyl, $NH_2$, $NH(C_{1-4}$alkyl$)$, $N(C_{1-4}$alkyl$)_2$, $C(O)OC_{1-4}$alkyl, $C(O)NH_2$, $C(O)NH(C_{1-4}$alkyl$)$, $C(O)N(C_{1-4}$alkyl$)_2$, $C(O)NHOH$, $C(O)NH(OC_{1-4}$alkyl$)$, $C(O)C_{1-4}$alkyl, $S(O)C_{1-4}$alkyl, $SO_2C_{1-4}$alkyl, $SO_2NHC_{1-4}$alkyl, $NHSO_2C_{1-4}$alkyl, $NHC(O)C_{1-4}$alkyl, CN, CH=NOH, CH=N($OC_{1-4}$alkyl), C($C_{1-4}$alkyl)=NOH, C($C_{1-4}$alkyl)=N($OC_{1-4}$alkyl), CH=NCN, CH=NC(O)$C_{1-4}$alkyl, CH=C(CN)$_2$, CH=CHNO$_2$, C(=NH)NH($C_{1-4}$alkyl), C($C_{1-4}$alkyl)=NCN, C($C_{1-4}$alkyl)=NC(O)$C_{1-4}$alkyl, C($C_{1-4}$alkyl)=C(CN)$_2$, or C($C_{1-4}$alkyl)=CHNO$_2$;

$R^4$ represents $C_{1-8}$alkyl, or $(CH_2)_n Ar-R^5$;

Ar represents a 4- to 8-membered hydrocarbon ring or an aromatic ring containing 0 to 4 heteroatoms;

$R^5$ represents H, or 1 to 4 same or different occurrences of F, $CF_3$, CN, Cl, $C_{1-4}$ alkyl, OH, $OC_{1-4}$alkyl, $NHC(O)C_{1-4}$alkyl, $NH_2$, $NH(C_{1-4}$ alkyl$)$, $N(C_{1-4}$alkyl$)_2$, $C(O)OC_{1-4}$alkyl, $OOCC_{1-4}$alkyl, $C(O)NH_2$, $C(O)NH(C_{1-4}$alkyl$)$, $C(O)N(C_{1-4}$alkyl$)_2$, $C(O)C_{1-4}$alkyl, $S(O)C_{1-4}$alkyl, $SO_2C_{1-4}$alkyl, $O_2CC_{1-4}$alkyl, E, or $W-(CH_2)_l E$;

E represents a 4- to 8-membered hydrocarbon ring or an aromatic ring containing 0 to 4 heteroatoms;

W represents O, S, NH, or $CH_2$;

l represents 0, 1, 2, 3, or 4;

m represents 0, 1, 2, 3, 4, 5, or 6; and n represents 0, 1, 2, 3, or 4;

the method comprising the steps of:

(1) contacting a compound of Formula (VII) or Formula (VIII) with a compound of Formula (IX) to obtain a compound of Formula (X) or Formula (XI),

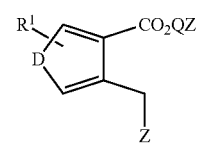

(VII)

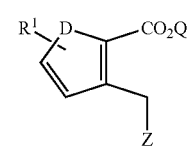

(VIII)

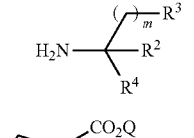

(IX)

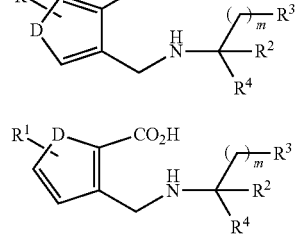

(X)

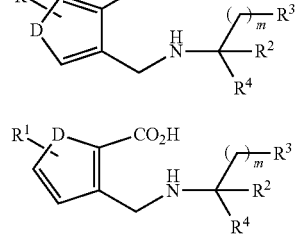

(XI)

wherein the definition of D, $R^1$, $R^2$, $R^3$, $R^4$ and more the same as that for Formula (I) or Formula (II), Z represents Cl, Br, I, Ms or Ts; and Q represents methyl or tert-butyl;

(2) hydrolyzing the compound of Formula (X) or Formula (XI) to obtain a corresponding acid of Formula (XII) or Formula (XIII)

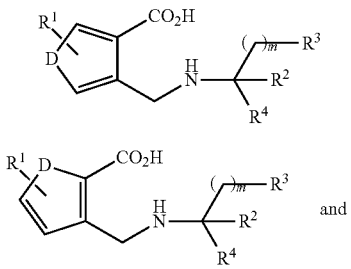

and (3) dehydrating and cyclizing the compound of Formula (XII) or Formula (XIII) to obtain the compound of Formula (I) or Formula (II).

17. A method of preparing a compound of Formula (I) or Formula (II) comprising contacting a compound of Formula (XIV) or Formula (XV)

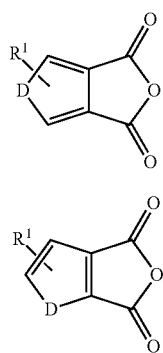

with a compound of Formula (IX) to obtain an intermediate compound, and then dehydrating and cyclizing the intermediate compound to give the compound of Formula (I) or Formula (II), wherein the definitions of D and $R^1$ are the same as that for Formula (I) or Formula (II).

18. The pharmaceutical composition of claim 12 further comprising a pharmaceutically acceptable carrier, excipient, filler, solvent, diluent, coloring agent, or adhesive, wherein the administration mode of the compound of Formula (I) or Formula (II) is selected from gastrointestinal administration, oral administration, intravenous injection, intraperitoneal injection, dermal injection, intramuscular injection, intranasal administration, intraocular administration, administration by inhalation, rectal administration, reproductive tract administration, or percutaneous absorption.

19. The compound of claim 1, wherein the compound is methyl 3-(3-ethoxy-4-methoxyphenyl)-3-(1-amino-4,6-dioxo-4H-thiophene[3,4-c]pyrrole-5(6H)-yl)propionate.

20. The compound of claim 1, wherein the compound is:
 (a) methyl 3-(3,4-dimethoxy-phenyl)-3-(4,6-dioxo-4H-thiophene[3,4-c]pyrrole-5(6H)-yl)propionate,
 (b) methyl 3-(3-ethoxy-4-methoxy-phenyl)-3-(4,6-dioxo-4H-thiophene[3,4-c]pyrrole-5(6H)-yl)propionate,
 (c) methyl 3-(3-propoxy-4-methoxy-phenyl)-3-(4,6-dioxo-4H-thiophene[3,4-c]pyrrole-5(6H)-yl)propionate,
 (d) methyl 3-(3-isopropoxy-4-methoxy-phenyl)-3-(4,6-dioxo-4H-thiophene[3,4-c]pyrrole-5(6H)-yl)propionate,
 (e) methyl 3-(3-cyclopentyloxy-4-methoxy-phenyl)-3-(4,6-dioxo-4H-thiophene[3,4-c]pyrrole-5(6H)-yl)propionate,
 (f) methyl 3-(3-benzyloxy-4-methoxy-phenyl)-3-(4,6-dioxo-4H-thiophene[3,4-c]pyrrole-5(6H)-yl)propionate,
 (g) methyl 3-(3-methoxy-4-ethoxy-phenyl)-3-(4,6-dioxo-4H-thiophene[3,4-c]pyrrole-5(6H)-yl)propionate,
 (h) methyl 3-(3-methoxy-4-propoxy-phenyl)-3-(4,6-dioxo-4H-thiophene[3,4-c]pyrrole-5(6H)-yl)propionate,
 (i) methyl 3-(3-methoxy-4-isopropoxy-phenyl)-3-(4,6-dioxo-4H-thiophene[3,4-c]pyrrole-5(6H)-yl)propionate,
 (j) methyl 3-(3-methoxy-4-cyclopentyloxy-phenyl)-3-(4,6-dioxo-4H-thiophene[3,4-c]pyrrole-5(6H)-yl)propionate,
 (k) methyl 3-(3-methoxy-4-benzyloxy-phenyl)-3-(4,6-dioxo-4H-thiophene[3,4-c]pyrrole-5(6H)-yl)propionate,
 (l) methyl 3-(4,6-dioxo-4H-thiophene[3,4-c]pyrrole-5(6H)-yl)-3-phenylpropionate,
 (m) methyl 3-(4-chlorophenyl)-3-(4,6-dioxo-4H-thiophene[3,4-c]pyrrole-5(6H)-yl)propionate,
 (n) methyl 3-(4-benzyloxy phenyl)-3-(4,6-dioxo-4H-thiophene[3,4-c]pyrrole-5(6H)-yl)propionate,
 (o) L-methyl 2-(4,6-dioxo-4H-thiophene[3,4-c]pyrrole-5(6H)-yl)-2-phenylacetate,
 (p) D-methyl 2-(4,6-dioxo-4H-thiophene[3,4-c]pyrrole-5(6H)-yl)-2-phenylacetate,
 (q) L-methyl 2-(4,6-dioxo-4H-thiophene[3,4-c]pyrrole-5(6H)-yl)-3-phenylpropionate,
 (r) methyl 3-(3-methyl-thiophene-2-yl)-3-(4,6-dioxo-4H-thiophene[3,4-c]pyrrole-5(6H)-yl)propionate,
 (s) ethyl 3-(3-ethoxy-4-methoxy-phenyl)-3-(4,6-dioxo-4H-thiophene[3,4-c]pyrrole-5(6H)-yl)propionate,
 (t) ethyl 3-(3-methoxy-4-ethoxy-phenyl)-3-(4,6-dioxo-4H-thiophene[3,4-c]pyrrole-5(6H)-yl)propionate,
 (u) methyl 3-(3,4-dimethoxy-phenyl)-3-(1-amino-4,6-dioxo-4H-thiophene[3,4-c]pyrrole-5(6H)-yl)propionate,
 (v) methyl 3-(3-ethoxy-4-methoxy-phenyl)-3-(1-amino-4,6-dioxo-4H-thiophene[3,4-c]pyrrole-5(6H)-yl)propionate,
 (w) methyl 3-(3-cyclopentyloxy-4-methoxy-phenyl)-3-(1-amino-4,6-dioxo-4H-thiophene[3,4-c]pyrrole-5(6H)-yl)propionate,
 (x) methyl 3-(3-methoxy-4-ethoxy-phenyl)-3-(1-amino-4,6-dioxo-4H-thiophene[3,4-c]pyrrole-5(6H)-yl)propionate,
 (y) methyl 3-(3-methoxy-4-propoxy-phenyl)-3-(1-amino-4,6-dioxo-4H-thiophene[3,4-c]pyrrole-5(6H)-yl)propionate,
 (z) methyl 3-(3-methoxy-4-benzyloxy-phenyl)-3-(1-amino-4,6-dioxo-4H-thiophene[3,4-c]pyrrole-5(6H)-yl)propionate,
 (aa) methyl 3-(3-cyclopentyloxy-4-methoxy-phenyl)-3-(1-acetylamino-4,6-dioxo-4H-thiophene[3,4-c]pyrrole-5(6H)-yl)propionate,
 (bb) methyl 3-(3-cyclopentyloxy-4-methoxy-phenyl)-3-(1-methylamino-4,6-dioxo-4H-thiophene[3,4-c]pyrrole-5(6H)-yl)propionate,
 (cc) 3-(3-methoxy-4-ethoxy-phenyl)-3-(4,6-dioxo-4H-thiophene[3,4-c]pyrrole-5(6H)-yl)propionitrile,
 (dd) 3-(3,4-dimethoxy-phenyl)-3-(4,6-dioxo-4H-thiophene[3,4-c]pyrrole-5(6H)-yl)propionitrile,
 (ee) 3-(3-methoxy-4-benzyloxy phenyl)-3-(4,6-dioxo-4H-thiophene[3,4-c]pyrrole-5(6H)-yl)propionitrile,
 (ff) 3-(3-ethoxy-4-methoxy phenyl)-3-(4,6-dioxo-4H-thiophene[3,4-c]pyrrole-5(6H)-yl)propionitrile, (gg) 3-(3-cyclopentyloxy-4-methoxy phenyl)-3-(4,6-dioxo-4H-thiophene[3,4-c]pyrrole-5(6H)-yl)propionitrile,
(hh) 3-(3-methoxy-4-ethoxy-phenyl)-3-(1-amino-4,6-dioxo-4H-thiophene[3,4-c]pyrrole-5(6H)-yl)propionitrile,
(ii) 3-(3,4-dimethoxy-phenyl)-3-(1-amino-4,6-dioxo-4H-thiophene[3,4-c]pyrrole-5(6H)-yl)propionitrile,
(jj) 3-(3-methoxy-4-benzyloxy phenyl)-3-(1-amino-4,6-dioxo-4H-thiophene[3,4-c]pyrrole-5(6H)-yl)propionitrile,
(kk) 3-(3-ethoxy-4-methoxy-phenyl)-3-(1-amino-4,6-dioxo-4H-thiophene[3,4-c]pyrrole-5(6H)-yl)propionitrile,
(ll) 3-(3-cyclopentyloxy-4-methoxy-phenyl)-3-(1-amino-4,6-dioxo-4H-thiophene[3,4-c]pyrrole-5(6H)-yl)propionitrile,
(mm) 3-(3-methoxy-4-benzyloxy phenyl)-3-(4,6-dioxo-4H-thiophene[3,4-c]pyrrole-5(6H)-yl)propionamide,
(nn) N-methyl 3-(3-methoxy-4-benzyloxy phenyl)-3-(4,6-dioxo-4H-thiophene[3,4-c]pyrrole-5(6H)-yl)propionamide,
(oo) N-ethyl 3-(3-methoxy-4-benzyloxy phenyl)-3-(4,6-dioxo-4H-thiophene[3,4-c]pyrrole-5(6H)-yl)propionamide,
(pp) N-phenyl 3-(3-methoxy-4-benzyloxy phenyl)-3-(4,6-dioxo-4H-thiophene[3,4-c]pyrrole-5(6H)-yl)propionamide,
(qq) N-benzyl 3-(3-ethoxy-4-methoxy-phenyl)-3-(4,6-dioxo-4H-thiophene[3,4-c]pyrrole-5(6H)-yl)propionamide,
(rr) 5-(1-(3-methoxy-4-ethoxy-phenyl)-3-hydroxypropyl)-5H-thiophene[3,4-c]pyrrole-4,6-dione,
(ss) 5-(1-(3-ethoxy-4-methoxy-phenyl)-3-hydroxypropyl)-5H-thiophene[3,4-c]pyrrole-4,6-dione,
(tt) 5-(1-(3-methoxy-4-benzyloxy phenyl)-3-oxo-3-(piperidine-1-yl)propyl)-5H-thiophene[3,4-c]pyrrole-4,6-dione,
(uu) N,N-dimethyl 3-(3-methoxy-4-benzyloxy phenyl)-3-(4,6-dioxo-4H-thiophene[3,4-c]pyrrole-5(6H)-yl)propionamide,
(vv) N,N-diethyl 3-(3-methoxy-4-benzyloxy phenyl)-3-(4,6-dioxo-4H-thiophene[3,4-c]pyrrole-5(6H)-yl)propionamide,
(ww) N-methyl-N-phenyl 3-(3-methoxy-4-benzyloxy phenyl)-3-(4,6-dioxo-4H-thiophene[3,4-c]pyrrole-5(6H)-yl)propionamide,
(xx) 5-(1-(3-methoxy-4-benzyloxy phenyl)-3-dimethylamino-propyl)-5H-thiophene[3,4-c]pyrrole-4,6-dione,
(yy) 5-(1-(3-Methoxy-4-benzyloxy phenyl)-3-diethylamino-propyl)-5H-thiophene[3,4-c]pyrrole-4,6-dione,
(zz) 5-(1-(3-methoxy-4-benzyloxy phenyl)-3-(piperidine-1-yl)propyl)-5H-thiophene[3,4-c]pyrrole-4,6-dione,
(aaa) 3-(3-ethoxy-4-methoxy-phenyl)-3-(4,6-dioxo-4H-thiophene[3,4-c]pyrrole-5(6H)-yl)propionic acid,
(bbb) 3-(3-methoxy-4-ethoxy-phenyl)-3-(4,6-dioxo-4H-thiophene[3,4-c]pyrrole-5(6H)-yl)propionic acid,
(ccc) 3-(3-methoxy-4-ethoxy-phenyl)-3-(4,6-dioxo-4H-thiophene[3,4-c]pyrrole-5(6H)-yl)-N-hydroxy propionamide,
(ddd) 3-(3-methoxy-4-ethoxy-phenyl)-3-(4,6-dioxo-4H-thiophene[3,4-c]pyrrole-5(6H)-yl)propionamide,
(eee) 5-(1-(3-ethoxy-4-methoxy-phenyl)-3-methoxy-propyl)-5H-thiophene[3,4-c]pyrrole-4,6-dione,
(fff) methyl 3-(3-ethoxy-4-methoxy-phenyl)-3-(4-oxo-4H-thiophene[3,4-c]pyrrole-5(6H)-yl)propionate,
(ggg) methyl 3-(3-methoxy-4-ethoxy-phenyl)-3-(4-oxo-4H-thiophene[3,4-c]pyrrole-5(6H)-yl)propionate,
(hhh) 3-(3-ethoxy-4-methoxy-phenyl)-3-(4-oxo-4H-thiophene[3,4-c]pyrrole-5(6H)-yl)propionitrile,
(iii) 3-(3-cyclopentyloxy-4-methoxy-phenyl)-3-(4-oxo-4H-thiophene[3,4-c]pyrrole-5(6H)-yl)propionitrile,
(jjj) 3-(3-methoxy-4-ethoxy-phenyl)-3-(4-oxo-4H-thiophene[3,4-c]pyrrole-5(6H)-yl)propionitrile,
(kkk) 3-(3-ethoxy-4-methoxy-phenyl)-3-(4,6-dioxo-4H-thiophene[3,4-c]pyrrole-5(6H)-yl)propyl-methyl sulfoxide,
(lll) 3-(3-ethoxy-4-methoxy-phenyl)-3-(4,6-dioxo-4H-thiophene[3,4-c]pyrrole-5(6H)-yl)propionaldehydeoxime methyl ether,
(mmm) 3-(3-ethoxy-4-methoxy-phenyl)-3-(4,6-dioxo-4H-thiophene[3,4-c]pyrrole-5(6H)-yl)butan-2-ol,
(nnn) 3-(3-ethoxy-4-methoxy-phenyl)-3-(4,6-dioxo-4H-thiophene[3,4-c]pyrrole-5(6H)-yl)butan-2-one, or
(ooo) methyl 3-(4-pyridyl)-3-(4,6-dioxo-4H-thiophene[3,4-c]pyrrole-5(6H)-yl)propionate.

* * * * *